United States Patent
Moskowitz et al.

(10) Patent No.: US 10,376,383 B2
(45) Date of Patent: *Aug. 13, 2019

(54) BI-DIRECTIONAL FIXATING/LOCKING TRANSVERTEBRAL BODY SCREW/INTERVERTEBRAL CAGE STAND-ALONE CONSTRUCTS

(71) Applicant: Moskowitz Family LLC, Rockville, MD (US)

(72) Inventors: Nathan C. Moskowitz, Rockville, MD (US); Mosheh T. Moskowitz, Rockville, MD (US); Ahmnon D. Moskowitz, Rockville, MD (US); Pablo A. Valdivia Y. Alvarado, Cambridge, MA (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,484

(22) Filed: Oct. 24, 2017

(65) Prior Publication Data

US 2018/0055651 A1    Mar. 1, 2018

Related U.S. Application Data

(60) Continuation of application No. 13/418,323, filed on Mar. 12, 2012, now Pat. No. 9,814,601, which is a
(Continued)

(51) Int. Cl.
*A61B 17/70* (2006.01)
*A61B 17/80* (2006.01)
(Continued)

(52) U.S. Cl.
CPC .......... *A61F 2/447* (2013.01); *A61B 17/7064* (2013.01); *A61B 17/8047* (2013.01);
(Continued)

(58) Field of Classification Search
CPC .............. A61F 2/447; A61F 2002/2835; A61F 2002/30476; A61F 2002/30772;
(Continued)

(56) References Cited

U.S. PATENT DOCUMENTS 2,360,942 A    10/1944    Ellerstein
4,064,881 A    12/1977    Meredith
(Continued)

FOREIGN PATENT DOCUMENTS

FR            2727003       5/1996
WO    WO 2004/0937 49    11/2004
WO    WO 2006/091503     8/2006

OTHER PUBLICATIONS

Dieter Grob et al., "Clinical Experience With the Dynesys Semirigid Fixation System for the Lumbar Spine," Spine, vol. 30, No. 3, 2005, pp. 324-331.
(Continued)

*Primary Examiner* — Pedro Philogene
(74) *Attorney, Agent, or Firm* — Fish & Richardson P.C.

(57) ABSTRACT

A bi-directional fixating transvertebral (BDFT) screw/cage apparatus is provided. The BDFT apparatus includes an intervertebral cage including a plurality of internal angled screw guides, a plurality of screw members, and a novel screw locking mechanism which consists of leaf springs which mechanically interact with BDFT screws which have ratcheted screw heads. The small leaf springs allow the ratchet teeth of the screw heads to rotate only in the penetrating direction. Due to the geometric orientation of the ratchet teeth vis-a-vis the adjacent spring leaf, rotation of the screw head in the opposite direction is prevented by the insertion of the string leaf in the space between the ratchet teeth (trough) of its final rotation. The uni-rotational interaction between the screw head-ratchet teeth/troughs and adjacent leaf spring is the mechanical basis for this novel
(Continued)

locking mechanism. The internal angled screw guides orient a first screw member superiorly and a second screw member inferiorly in some embodiments, and orient a second screw member and a third screw member superiorly, and a first screw member and fourth screw member inferiorly in other embodiments. The intervertebral cage is adapted for posterior lumbar intervertebral placement, anterior lumbar intervertebral placement, anterio-lateral thoracic intervertebral placement, or anterior cervical intervertebral placement.

24 Claims, 25 Drawing Sheets

Related U.S. Application Data continuation-in-part of application No. 13/103,994, filed on May 9, 2011, now Pat. No. 9,603,713, which is a division of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 13/418,323 is a continuation-in-part of application No. 13/084,543, filed on Apr. 11, 2011, now Pat. No. 8,353,913, which is a division of application No. 11/842,855, filed on Aug. 21, 2007, now Pat. No. 7,942,903, said application No. 13/418,323 is a continuation-in-part of application No. 13/401,829, filed on Feb. 21, 2012, now Pat. No. 9,744,052.

(60) Provisional application No. 61/451,582, filed on Mar. 11, 2011, provisional application No. 61/451,579, filed on Mar. 10, 2011, provisional application No. 61/445,034, filed on Feb. 21, 2011, provisional application No. 60/670,231, filed on Apr. 12, 2005.

(51) Int. Cl.
*A61B 17/86* (2006.01)
*A61B 17/92* (2006.01)
*A61F 2/28* (2006.01)
*A61F 2/30* (2006.01)
*A61F 2/44* (2006.01)

(52) U.S. Cl.
CPC .... *A61B 17/8605* (2013.01); *A61B 2017/922* (2013.01); *A61F 2002/2835* (2013.01); *A61F 2002/30476* (2013.01); *A61F 2002/30772* (2013.01); *A61F 2002/30787* (2013.01); *A61F 2002/448* (2013.01); *A61F 2002/4475* (2013.01); *A61F 2220/0025* (2013.01)

(58) Field of Classification Search
CPC .... A61F 2002/30787; A61F 2002/4475; A61F 2002/448; A61F 2220/0025; A61B 17/7064; A61B 17/8047; A61B 17/8605; A61B 2017/922
USPC .......... 623/17.11–17.16; 606/246–279, 144, 606/151, 86 A, 300–308, 329
See application file for complete search history.

(56) References Cited

U.S. PATENT DOCUMENTS

| | | |
|---|---|---|
| 4,554,914 A | 11/1985 | Kapp et al. |
| 4,599,086 A | 7/1986 | Doty |
| 4,636,217 A | 1/1987 | Ogilvie et al. |
| 4,904,261 A | 2/1990 | Dove et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | Macmillan et al. |
| 5,123,926 A | 6/1992 | Pisharodi |
| 5,290,312 A | 3/1994 | Kojimoto et al. |
| 5,405,391 A | 4/1995 | Henderson et al. |
| 5,413,583 A | 5/1995 | Wohlers |
| 5,454,819 A | 10/1995 | Knoepfler |
| 5,514,180 A | 5/1996 | Heggeness et al. |
| 5,660,188 A | 8/1997 | Groiso |
| 5,667,472 A | 9/1997 | Finn et al. |
| 5,713,912 A | 2/1998 | Porter |
| 5,782,832 A | 7/1998 | Larsen et al. |
| 5,865,848 A | 2/1999 | Baker |
| 5,888,223 A | 3/1999 | Bray, Jr. |
| 5,916,224 A | 6/1999 | Esplin |
| 5,951,574 A | 9/1999 | Stefanchik et al. |
| 5,960,522 A | 10/1999 | Boe |
| 5,968,054 A | 10/1999 | Yeatts et al. |
| 5,976,136 A | 11/1999 | Bailey et al. |
| 6,126,689 A | 10/2000 | Brett |
| 6,224,602 B1 | 5/2001 | Hayes |
| 6,235,034 B1 | 5/2001 | Bray |
| 6,322,562 B1 | 11/2001 | Wolter |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,572,653 B1 | 6/2003 | Simonson |
| 6,579,318 B2 | 6/2003 | Varga et al. |
| 6,582,468 B1 | 6/2003 | Gauchet |
| 6,613,055 B2 | 9/2003 | Di Emidio |
| 6,629,998 B1 | 10/2003 | Lin |
| 6,641,614 B1 | 11/2003 | Wagner et al. |
| 6,655,243 B2 | 12/2003 | Anderson et al. |
| 6,719,794 B2 | 4/2004 | Gerber |
| 6,723,126 B1 | 4/2004 | Berry |
| 6,733,532 B1 | 5/2004 | Gauchet et al. |
| 6,764,491 B2 | 7/2004 | Frey et al. |
| 6,770,094 B2 | 8/2004 | Fehling et al. |
| 6,824,564 B2 | 11/2004 | Crozet |
| 6,852,117 B2 | 2/2005 | Orlowski |
| 6,890,355 B2 | 5/2005 | Michelson |
| 6,904,308 B2 | 6/2005 | Frisch et al. |
| 6,953,477 B2 | 10/2005 | Berry |
| 6,955,671 B2 | 10/2005 | Uchikubo |
| 6,972,019 B2 | 12/2005 | Michelson |
| 6,974,480 B2 | 12/2005 | Messerli et al. |
| 7,030,904 B2 | 4/2006 | Adair et al. |
| 7,033,394 B2 | 4/2006 | Michelson |
| 7,037,258 B2 | 5/2006 | Chatenever et al. |
| 7,077,864 B2 | 7/2006 | Byrd et al. |
| 7,097,615 B2 | 8/2006 | Banik et al. |
| 7,135,043 B2 | 11/2006 | Nakahara et al. |
| 7,211,112 B2 | 5/2007 | Baynham et al. |
| 7,232,464 B2 | 6/2007 | Mathieu et al. |
| 7,238,203 B2 | 7/2007 | Bagga et al. |
| 7,326,248 B2 | 2/2008 | Michelson |
| 7,442,209 B2 | 10/2008 | Michelson |
| 7,442,299 B2 | 10/2008 | Lee et al. |
| 7,615,059 B2 | 11/2009 | Watschke et al. |
| 7,618,456 B2 | 11/2009 | Mathieu et al. |
| 7,628,816 B2 | 12/2009 | Magerl et al. |
| 7,704,279 B2 | 4/2010 | Moskowitz et al. |
| 7,727,246 B2 | 6/2010 | Sixto et al. |

(56) References Cited

U.S. PATENT DOCUMENTS

| | | | |
|---|---|---|---|
| 7,776,093 | B2 | 8/2010 | Wolek et al. |
| 7,803,162 | B2 | 9/2010 | Marnay et al. |
| 7,846,207 | B2 | 12/2010 | Lechmann et al. |
| 7,862,616 | B2 | 1/2011 | Lechmann et al. |
| 7,875,076 | B2 | 1/2011 | Mathieu et al. |
| 7,887,591 | B2 | 2/2011 | Aebi et al. |
| 7,942,903 | B2 | 5/2011 | Moskowitz et al. |
| 7,959,675 | B2 | 6/2011 | Gately |
| 7,972,363 | B2 | 7/2011 | Moskowitz et al. |
| 8,029,512 | B2 | 10/2011 | Paltzer |
| 8,034,060 | B2 | 10/2011 | Keren et al. |
| 8,105,367 | B2 | 1/2012 | Austin et al. |
| 8,114,162 | B1 | 2/2012 | Bradley |
| 8,137,405 | B2 * | 3/2012 | Kostuik .................. A61F 2/447 606/287 |
| 8,167,949 | B2 | 5/2012 | Tyber et al. |
| 8,268,000 | B2 | 9/2012 | Waugh et al. |
| 8,328,872 | B2 | 12/2012 | Duffield et al. |
| 8,353,913 | B2 * | 1/2013 | Moskowitz ........ A61B 17/0642 606/86 A |
| 8,403,986 | B2 | 3/2013 | Michelson |
| 8,414,651 | B2 | 4/2013 | Tyber et al. |
| 8,419,797 | B2 | 4/2013 | Biedermann et al. |
| 8,425,607 | B2 | 4/2013 | Waugh et al. |
| 8,540,774 | B2 | 9/2013 | Kueenzi et al. |
| 8,613,761 | B2 * | 12/2013 | Lindemann ........ A61B 17/7059 606/289 |
| 8,728,165 | B2 | 5/2014 | Parry et al. |
| 8,882,813 | B2 | 11/2014 | Jones et al. |
| 9,814,601 | B2 * | 11/2017 | Moskowitz ............. A61F 2/447 |
| 2002/0068977 | A1 | 6/2002 | Jackson |
| 2002/0143338 | A1 | 10/2002 | Orbay et al. |
| 2003/0130737 | A1 | 7/2003 | McGahan et al. |
| 2004/0088054 | A1 | 6/2004 | Berry |
| 2004/0177531 | A1 | 9/2004 | Dibenedetto et al. |
| 2004/0193272 | A1 | 9/2004 | Zubok et al. |
| 2004/0220571 | A1 | 11/2004 | Assaker et al. |
| 2004/0254644 | A1 | 12/2004 | Taylor |
| 2005/0027362 | A1 | 2/2005 | Williams et al. |
| 2005/0049590 | A1 | 3/2005 | Alleyne et al. |
| 2005/0177235 | A1 | 8/2005 | Baynham et al. |
| 2005/0216084 | A1 | 9/2005 | Fleischmann |
| 2005/0273170 | A1 | 12/2005 | Navarro et al. |
| 2005/0278026 | A1 | 12/2005 | Gordon et al. |
| 2006/0155285 | A1 | 7/2006 | Anderson |
| 2007/0213820 | A1 | 9/2007 | Magerl et al. |
| 2007/0250167 | A1 | 10/2007 | Bray et al. |
| 2007/0276498 | A1 | 11/2007 | Aebi et al. |
| 2008/0183293 | A1 | 7/2008 | Parry et al. |
| 2008/0249569 | A1 | 10/2008 | Waugh et al. |
| 2008/0249575 | A1 * | 10/2008 | Waugh .................... A61F 2/447 606/305 |
| 2008/0249625 | A1 | 10/2008 | Waugh et al. |
| 2008/0281424 | A1 | 11/2008 | Parry et al. |
| 2008/0281425 | A1 | 11/2008 | Thalgott et al. |
| 2009/0030520 | A1 | 1/2009 | Biedermann et al. |
| 2009/0080997 | A1 | 3/2009 | Johnson |
| 2009/0105830 | A1 | 4/2009 | Jones et al. |
| 2009/0105831 | A1 | 4/2009 | Jones et al. |
| 2009/0182430 | A1 | 7/2009 | Tyber et al. |
| 2009/0187218 | A1 | 7/2009 | Schaffhausen |
| 2009/0210062 | A1 * | 8/2009 | Thalgott ............... A61F 2/4465 623/17.16 |
| 2010/0145460 | A1 * | 6/2010 | McDonough ...... A61B 17/1728 623/17.16 |
| 2010/0305704 | A1 | 12/2010 | Messerli et al. |
| 2012/0271423 | A1 | 10/2012 | Wallenstein et al. |
| 2012/0277870 | A1 | 11/2012 | Wolters et al. |
| 2012/0323330 | A1 | 12/2012 | Kueenzi et al. |
| 2013/0060339 | A1 | 3/2013 | Duffield et al. |
| 2013/0073044 | A1 | 3/2013 | Gamache |

OTHER PUBLICATIONS

Vincent C. Traynelis. "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. To Aug. 1, 2003, pp. S15-S23.

International Search Report (ISR) and Written Opinion of the International Searching Authority, dated Dec. 3, 2007, International Application No. PCT/US 07/05005.

International Search Report (ISR) and Written Opinion of the International Searching Authority, dated Jul. 9, 2008, International Application No. PCT/US2007/021013.

International Search Report (ISR) and Written Opinion of the International Searching Authority, dated May 21, 2008, International Application No. PCT/US2007/021015.

* cited by examiner

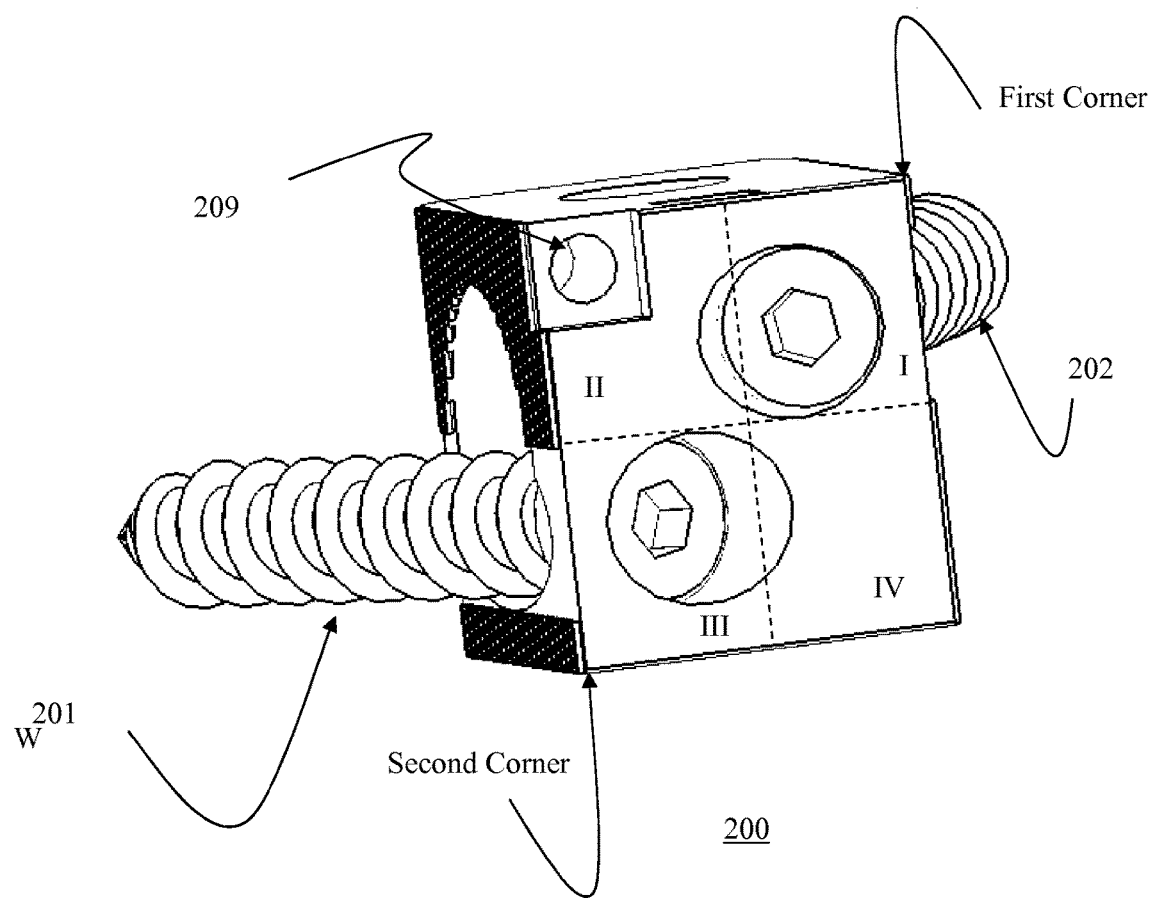
Fig. 5C(ii)

BI-DIRECTIONAL FIXATING/LOCKING TRANSVERTEBRAL BODY SCREW/INTERVERTEBRAL CAGE STAND-ALONE CONSTRUCTS

This application is a Continuation of U.S. patent application Ser. No. 13/418,323, filed Mar. 12, 2012, which is a Continuation-In-Part Application, for which priority is claimed under 35 U.S.C. § 120, of copending U.S. patent application Ser. No. 13/103,994, filed on May 9, 2011, which is a Divisional of U.S. patent application Ser. No. 12/054,335, filed on Mar. 24, 2008 (now U.S. Pat. No. 7,972,363 B2, issued on Jul. 5, 2011), which is a Continuation-In-Part of application Ser. No. 11/842,855, filed on Aug. 21, 2007 (now U.S. Pat. No. 7,942,903, issued May 17, 2011), which is a Continuation-In-Part of application Ser. No. 11/536,815, filed on Sep. 29, 2006 (now U.S. Pat. No. 7,846,188 B2, issued Dec. 7, 2010), which is a Continuation-In-Part of application Ser. No. 11/208,644, filed on Aug. 23, 2005 (now U.S. Pat. No. 7,704,279 issued on Apr. 27, 2010), the entire contents of all of the above identified patent applications are hereby incorporated by reference in their entirety and for which priority of each of the above-identified applications is claimed under 35 U.S.C. § 120.

This application is a Continuation of U.S. patent application Ser. No. 13/418,323, filed Mar. 12, 2012, which is also a Continuation-In-Part Application, for which priority is claimed under 35 U.S.C. § 120, of copending application Ser. No. 13/084,543, filed on Apr. 11, 2011, which is a Divisional of application Ser. No. 11/842,855, filed on Aug. 21, 2007 (now U.S. Pat. No. 7,942,903, issued May 17, 2011), which is a Continuation-In-Part of application Ser. No. 11/536,815, filed on Sep. 29, 2006 (now U.S. Pat. No. 7,846,188 B2, issued Dec. 7, 2010), which is a Continuation-In-Part of application Ser. No. 11/208,644, filed on Aug. 23, 2005 (now U.S. Pat. No. 7,704,279 issued on Apr. 27, 2010), the entire contents of all of the above identified patent applications are hereby incorporated by reference in their entirety and for which priority of each of the above-identified applications is claimed under 35 U.S.C. § 120.

This application is a Continuation of U.S. patent application Ser. No. 13/418,323, filed Mar. 12, 2012, which is also a Continuation-In-Part Application, for which priority is claimed under 35 U.S.C. § 120, of copending application Ser. No. 13/401,829, filed on Feb. 21, 2012, which claims priority under 35 U.S.C. § 119(e) of U.S. Provisional Application No. 61/445,034, filed on Feb. 21, 2011, the entire contents of all of the above identified patent applications are hereby incorporated by reference in their entirety.

This application is a Continuation of U.S. patent application Ser. No. 13/418,323, filed Mar. 12, 2012, which is also claims priority under 35 U.S.C. § 119(e) of U.S. Provisional Application No. 61/451,582, filed on Mar. 10, 2011, U.S. Provisional Application No. 61/451,579, filed on Mar. 10, 2011, and U.S. Provisional Application No. 61/445,034, filed on Feb. 21, 2011, the entire contents of all of the above identified patent applications are hereby incorporated by reference in their entirety.

U.S. patent application Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, each claim the benefit of priority under 35 U.S.C. § 119(e) of U.S. Provisional Application No. 60/670,231, filed on Apr. 12, 2005, and this application hereby incorporates the claim of priority to this provisional application under 35 U.S.C. § 119(e) from the aforementioned intermediate applications (for which priority of each intermediate application is claimed under 35 U.S.C. § 120); and the entire contents of all of the above identified patent applications are hereby incorporated by reference in their entirety.

FIELD OF DISCLOSURE

The present invention relates to a unique universal bi-directional screw (BDS) system, and in particular its application to the spine, also referred to as bi-directional fixating transvertebral (BDFT) screw/cage constructs which can be used as stand-alone intervertebral devices which combine the dual functions of an intervertebral spacer that can be filled with bone fusion material(s), as well as a bi-directional transvertebral bone fixating/fusion screw apparatus. In the posterior lumbosacral and thoracic spine, intervertebral cage/BDFT screw constructs can be used as stand-alone devices obviating the need for pedicle screw fixation in many but not all cases. In the anterior cervical, thoracic and lumbosacral spine, intervertebral cage/BDFT screw constructs can be used as stand-alone devices obviating the need for anterior or lateral (thoracic and lumbosacral) spinal plating, and/or supplemental posterior pedicle screw fixation.

BACKGROUND

The history and evolution of instrumented spinal fusion in the entire human spine has been reviewed in related application Ser. No. 12/054,335, filed on Mar. 24, 2008, Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, the contents of which are hereby incorporated by reference in their entirety. Conventionally, the majority of posterior cervical and almost all posterior thoracic and lumbosacral fusion surgical techniques are typically supplemented with pedicle screw placement. Conventionally, the majority of anterior cervical spinal fusions, and many anterio-lateral thoracic, and anterior or anterio-lateral lumbosacral fusions are supplemented with anterior or anterior-lateral spinal plating, and very often, in particular in the thoracic and lumbosacral spine, are supplemented with posterior pedicle screw instrumentation.

Complications of pedicle screw placement in cervical, thoracic and lumbosacral spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations. Recent advances in pedicle screw fixation including minimally invasive, and stereotactic CT image-guided technology, and the development of flexible rods, imperfectly address some but not all of these issues.

Complications of anterior plating in the cervical spine include potential plate, and/or screw esophageal compression, and misplaced screws leading to neurovascular injury. Complications of anterior or anterior-lateral plating in the anterior lumbar spine include potential devastating injury to the major vessels due to chronic vascular erosion of the major vessels, or acute vascular injuries due to partial or complete plate and/or screw back out. Furthermore, for re-do surgeries, plate removal can be arduous, with potential complications of prolonged esophageal retraction, vascular injury and screw breakage. Recent advances including diminishing the plate width and/or profile, and absorbable plates, imperfectly address some but not all of these issues.

Complications of all conventional spinal anterior intervertebral device constructs are their potential for extrusion in the absence of plating. Hence, they are supplemented with anterior plating to prevent extrusion. Complications of posterior lumbosacral intervertebral device construct in the presence or absence of supplemental pedicle screw fixation is device extrusion, and potential nerve root and/or vascular injuries.

SUMMARY

Herein described are multiple exemplary embodiments of a device which combines in a single stand-alone construct the dual functions of: a) an intervertebral cage spacer which can be filled with bone fusion material maintaining disc height, and, b) a bi-directional fixating/fusion transvertebral body screw apparatus. These embodiments are described for posterior and anterior lumbar (and anterio-lateral thoracic) intervertebral placement, and anterior cervical intervertebral placement. The present invention recognizes the aforementioned problems with prior art apparatus and solves these problems by, among other things, improving upon the designs illustrated in the aforementioned related applications. The present application provides an advanced and novel bi-directional fixating transvertebral (BDFT) screw/cage apparatus with a modified novel cage which has indentations on the upper aspect of the screw box adjacent to the internalized angled screw guides. These indentations have leaf springs which are press fit into these indentations. The leaf springs function as screw locking mechanisms in conjunction with specialized BDFT screws that are designed with ratcheted screw heads. The small leaf springs which are perpendicularly aligned with the screw head ratchet spiked teeth and troughs allow the ratchet teeth of the screw heads to rotate only in the penetrating direction. Due to the geometric orientation of the ratchet teeth and troughs vis-à-vis the spring leaf, rotation of the screw head in the opposite direction is prevented. The spring leaf engages the space between the ratchet teeth (troughs) upon its final allowed turn, and prevents any rotation in the opposite direction thereby locking the screw into its final position. The interaction between the adjacent leaf springs and the screws ratcheted teeth and troughs which only allow screw rotation in the penetrating direction is the mechanical basis for this novel locking mechanism. This mechanism can be used not only for these constructs but also with any other device which requires a locking screw. All these novel modifications improve the probability of a solid fusion with this new invention.

The exemplary embodiments of a bi-directional fixating transvertebral (BDFT) screw/cage apparatus provide as strong or stronger segmental fusion as pedicle screws without the complications arising from pedicle screw placement, which include misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns and not the vertebral bodies via the transpedicular route thereby excluding the posterior spinal column, then healthy facet joints, if they exist, are preserved. Because the present invention accomplishes both anterior and middle column fusion, without rigidly fixating the posterior column, the present invention in essence creates a flexible fusion.

The present invention recognizes that the very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss and significant reduction in operating room (O.R.) time. Thus, the complication of pedicle screw pull out, and hence, high re-operation rate associated with the current embodiment of flexible fusion pedicle screws/rods is obviated. The lumbosacral intervertebral cage/BDFT screw constructs can be introduced via posterior, lateral, transforaminal or anterior interbody fusion approaches/surgical techniques. Although one can opt to supplement these constructs with transpedicular screws there would be no absolute need for supplemental pedicle screw fixation with these operative techniques.

The anterior placement of a bi-directional fixating transvertebral (BDFT) screw/cage apparatus according to the embodiments of the present invention into the cervical and lumbar spine obviates the need for supplemental anterior cervical or anterior lumbar plating. The sole purpose of these plates is to prevent intervertebral device extrusion. This function is completely obviated and replaced by the dual functioning bi-directional fixating transvertebral (BDFT) screw/cage apparatus, according to the present invention. The obvious advantage of this is a significant savings in operative time, and prevention of injuries associated with plating, in particular esophageal, large and small vessel injuries, and spinal cord nerve root injuries.

Because the embodiments of the bi-directional fixating transvertebral (BDFT) screw/cage apparatus engage a small percentage of the rostral and caudal vertebral body surface area, multi-level fusions can be performed with these devices.

Conventionally, failed anterior lumbar arthroplasties are salvaged by combined anterior and posterior fusions. Intervertebral cage/BDFT screw constructs may be utilized as a one-step salvage mechanism for failed/extruded anteriorly placed lumbar artificial discs obviating the need for supplemental posterior pedicle screws and/or anterior lumbar plating thereby significantly reducing and/or eliminating co-morbidities associated with these other salvage procedures.

Likewise, anterior cervical intervertebral cage/BDFT screw construct placement can be used to salvage failed anterior cervical arthroplasties, and re-do fusions without having to supplement with cervical anterior plates, thereby reducing the morbidity of this procedure.

In addition, if a patient develops a discogenic problem necessitating anterior cervical discectomy and fusion at a level above or below a previously fused and plated segment, the present invention reduces or eliminates the need to remove the prior plate in order to place a new superior plate, because the function of the plate is replaced by the dual functioning intervertebral cervical construct, thereby reducing the operating room time and surgical morbidity of this procedure.

Furthermore, because of the orientation and length of the BDFT screws within the intervertebral cage/BDFT constructs, multiple level fusions can be easily performed.

For example, an exemplary embodiment is directed to an intervertebral cage spacer and bi-directional fixating/fusion transvertebral body screw/cage apparatus. The apparatus includes an intervertebral cage for maintaining disc height.

The intervertebral cage includes a first internal screw guide and a second internal screw guide adjacent to novel cage indentations which contains a press-fit leaf spring. The apparatus further includes a first screw member having a screw head with ratchet teeth, a tapered end and a threaded body disposed within the intervertebral cage, a second screw member having a screw head with ratchet teeth, a tapered end and a threaded body disposed within the intervertebral cage, and a first screw locking mechanism that prevents the first screw member and the second screw from pulling-out of the first internal screw guide and the second internal screw guide.

Another exemplary embodiment is directed to an integral intervertebral cage spacer and bi-directional fixating/fusion transvertebral body screw apparatus, including an intervertebral cage having a plurality of internal angled screw guides. The apparatus further includes a plurality of screw members having a screw head with ratchet teeth and troughs, a tapered end and a threaded body disposed within the plurality of internal angled screw guides of the intervertebral cage, which are adjacent to novel cage indentations which contain press fit leaf springs. Due to the geometric orientation of the ratchet teeth on the screw head, the adjacent leaf springs allow the screws to rotate only in the penetrating direction. Screw rotation in the opposite, back out, direction is prevented because the leaf spring engages the space in between the ratchet teeth (troughs) preventing this opposite rotation and hence locking it preventing the plurality of screw members from pulling out of the plurality of internal angled screw guides.

Another exemplary embodiment is directed to a method of inserting a bi-directional fixating transvertebral (BDFT) screw/cage apparatus between a first vertebral body and a second vertebral body. The method includes measuring a dimension of a disc space between the first vertebral body and the second vertebral body, determining that the disc space is a posterior or lateral lumbar disc space, an anterior lumbar disc space, or an anterior cervical disc space, selecting an intervertebral cage based on the measured dimension of the disc space and based on the determination of the disc space being the posterior lumbar disc space, the lateral lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by its final turn when it's flush with the surface of the cage. The leaf spring prevents screw back out or pull out by engaging and locking the space between the ratchet teeth (troughs) of the screw head when the screws are in their final resting positions.

The posterior lumbar BDFT cage screw apparatus is uniquely designed in order to get into the posterior space and obtain proper screw angulations. Two exemplary embodiments are described; one that is rectangular and one that is elliptical and concave mimicking the posterior intervertebral disc space. In both exemplary embodiments, the axes of the internal screw guides are not horizontally aligned as they are in the cervical embodiment. Their axes must be oblique one to the other, and the screw guides must be very close to one another, in order for the screws to achieve proper vertebral body penetration in such a restricted posterior lumbar inter space.

In the embodiments having an anterior lumbar embodiment four screw design, in order to achieve maximal stability and to prevent subsidence, the lateral two screws penetrate the inferior vertebral body, and the middle two screws project to the superior vertebral body.

In all BDFT embodiments, the screw angle guides have an approximate twenty five degree angle. The angles can be variable or divergent.

In all embodiments the screw drill guide narrows such that the screw head is countersunk into the cage and thus it can be locked even in the absence of an additional screw locking mechanism. The screw locking mechanism described herein is yet an additional mechanism preventing screw back out.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE EXEMPLARY EMBODIMENTS

Figure 1A:
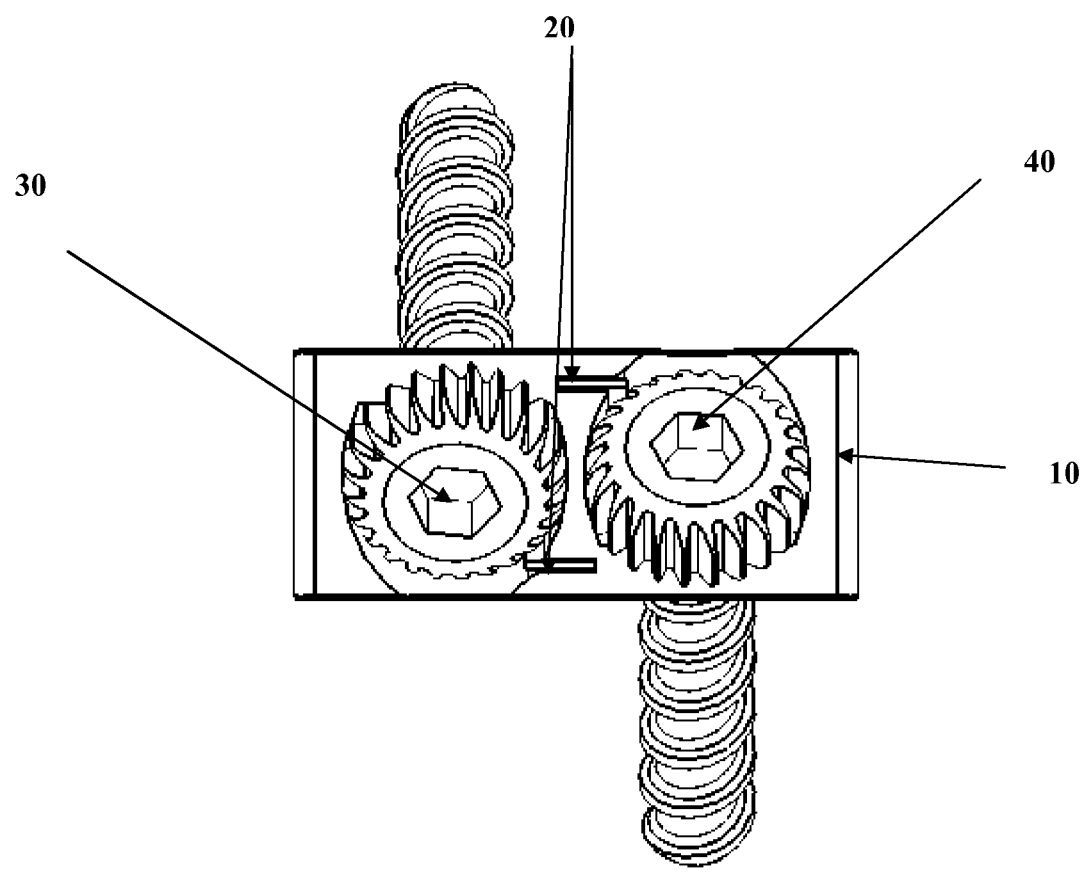
FIG. 1A illustrates a top view of an anterior cervical intervertebral cage/BDFT screw construct according to an embodiment of the invention.
Figure 1B:
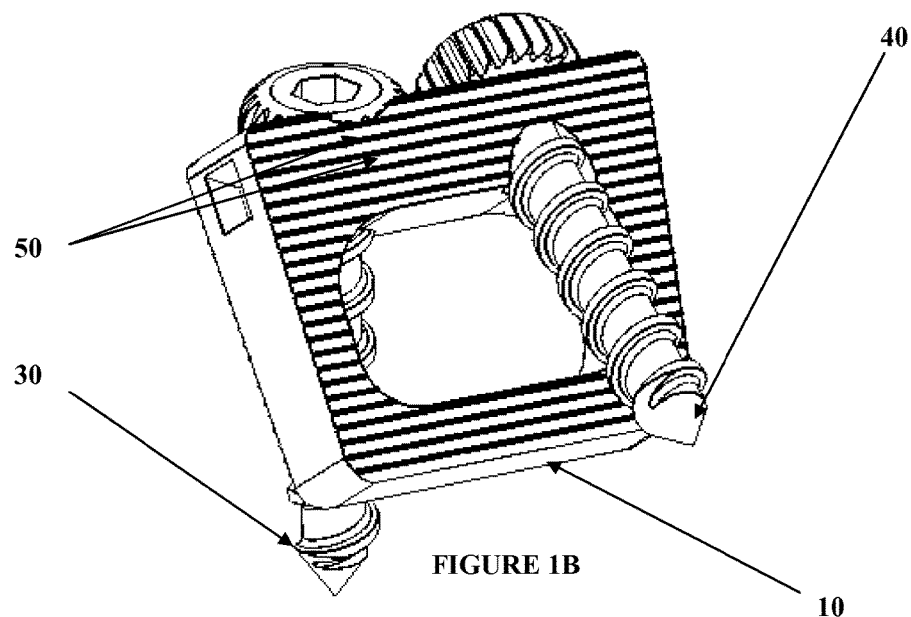
FIG. 1B illustrates a bottom perspective (isometric) view of an anterior cervical intervertebral cage/BDFT screw construct according to an embodiment of the invention.
Figure 1C:
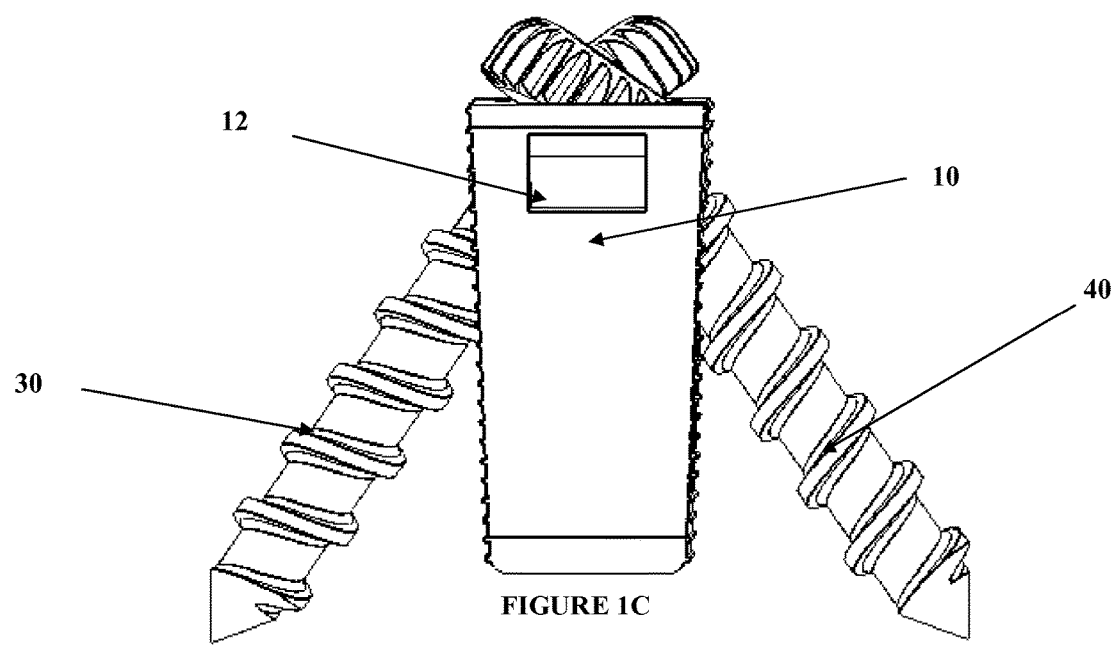
FIG. 1C illustrates a side view of an anterior cervical intervertebral cage/BDFT screw construct according to an embodiment of the invention.
Figure 1D:
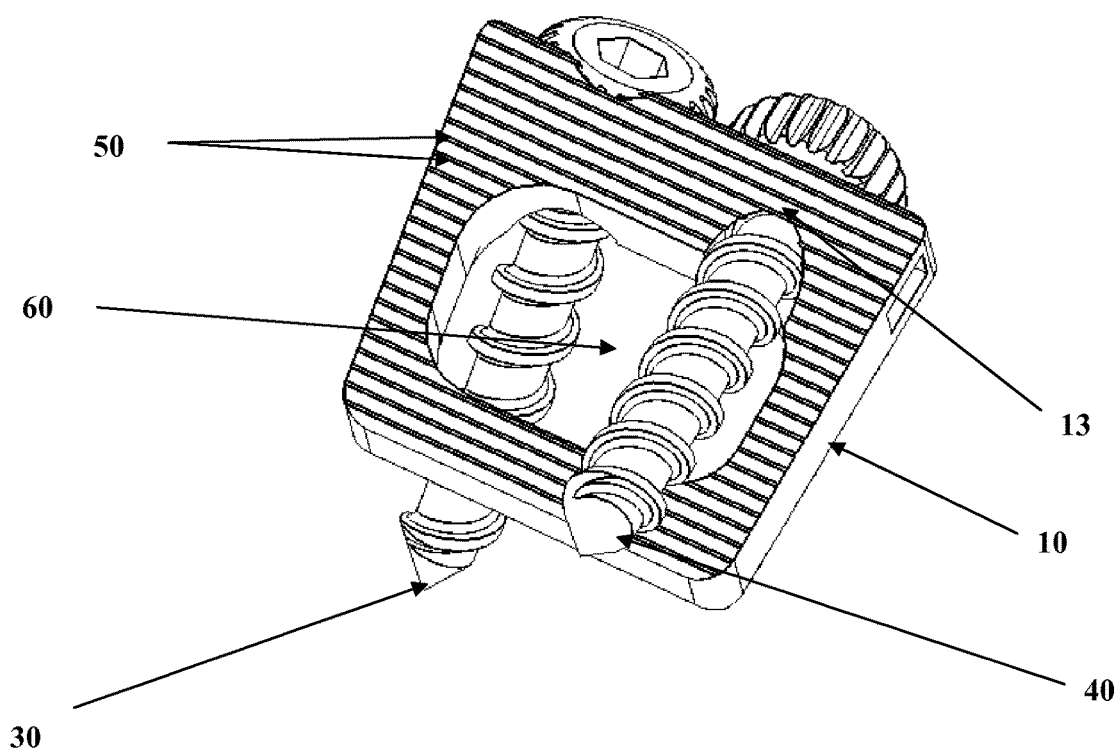
FIG. 1D illustrates a bottom, perspective view of an anterior cervical intervertebral cage/BDFT screw construct according to an embodiment of the invention.
Figure 1E:
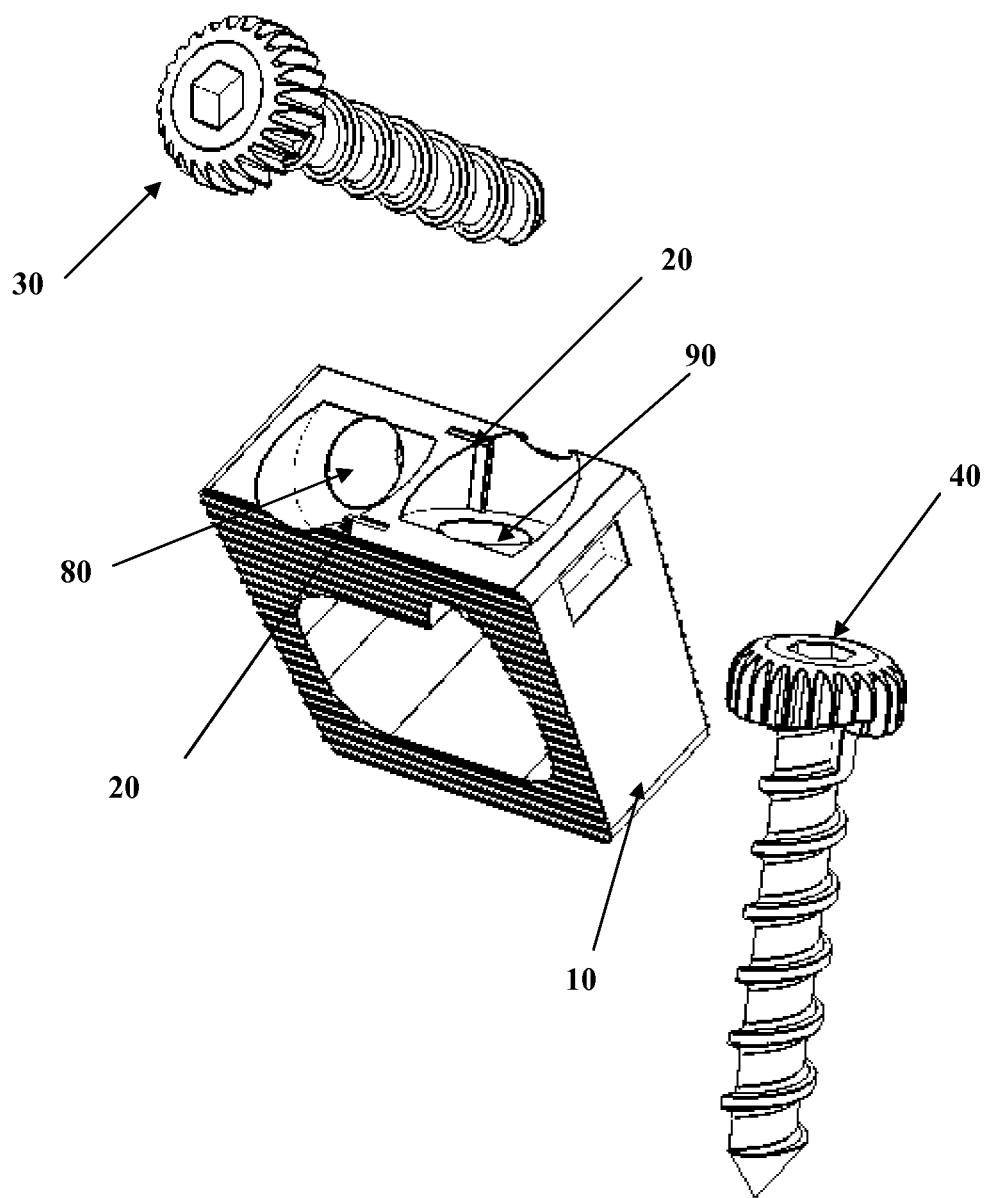
FIG. 1E illustrates a front, perspective, exploded view of an anterior cervical intervertebral cage/BDFT screw construct according to an embodiment of the invention.
Figure 1F:
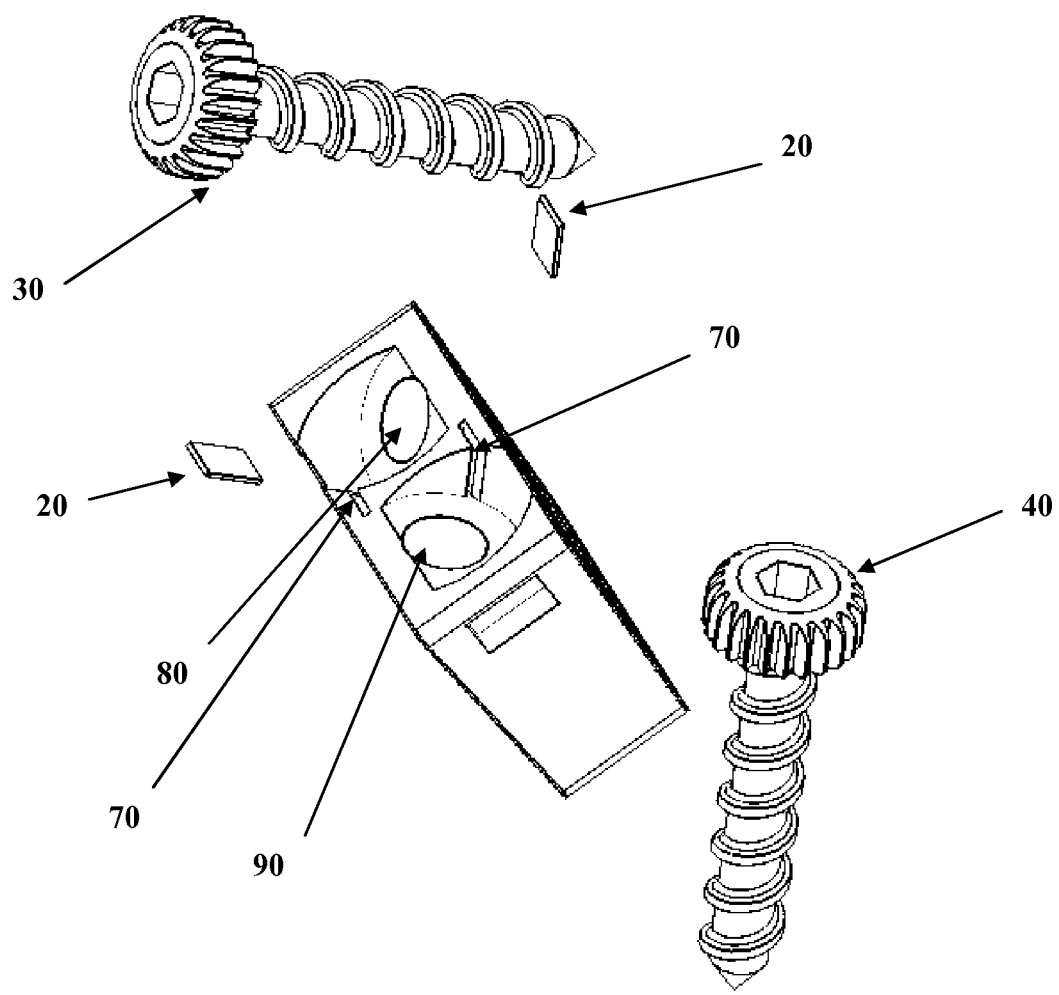
FIG. 1F illustrates a top, perspective exploded view of an anterior cervical intervertebral cage/BDFT screw construct according to an embodiment of the invention.
Figure 1G:
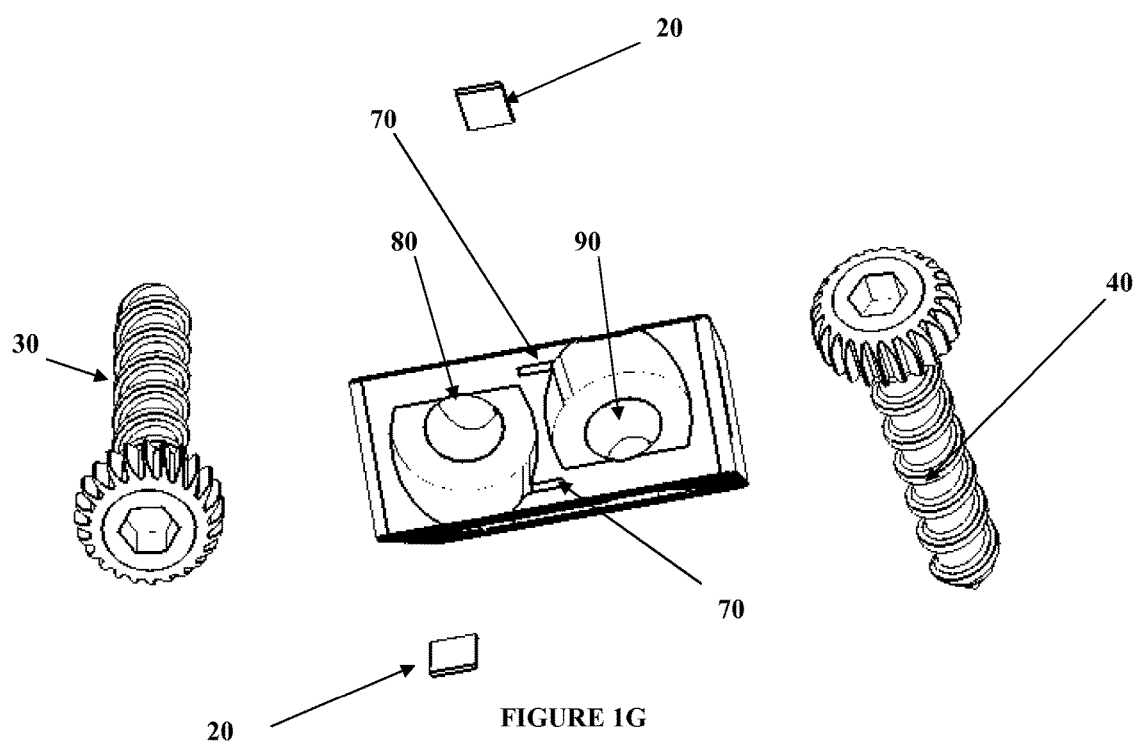
FIG. 1G illustrates a top, perspective exploded view of an anterior cervical intervertebral cage/BDFT screw construct with visualized internalized angled screw guides according to an embodiment of the invention.

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-5E, exemplary embodiments of the invention will now be described.

1. Exemplary Medical Device

Referring to FIGS. 1A-5E the above described problems of the conventional art can be solved in the cervical, thoracic and lumbosacral spines by insertion into the denuded intervertebral disc space multiple embodiments of a bi-directional fixating transvertebral (BDFT) screw/cage apparatus.

For example, FIGS. 1A-1G illustrate three-dimensional views of an exemplary embodiment of an anterior cervical intervertebral cage/BDFT construct 10. In this embodiment, the top portion of the cage 10 has indentations 70 that are adjacent to the internalized screw guides 80, 90 (FIG. 1F) which contain press-fit leaf spring screw locking mechanisms 20. The cage 10 also includes additional indentations 12 on the side surfaces of the cage 10 for insertion of the prongs of an insertion device. In an exemplary embodiment, a side surface of the cage 10 can elliptically contoured when viewed from the side (FIG. 1C) to fit into the bi-concave cervical disc space. The embodiment includes two screws 30, 40. The screws 30, 40 include screw heads with ratchet teeth. The teeth have troughs in between. A first screw 30 is oriented rostrally (superiorly) and a second screw 40 is oriented caudally (inferiorly). The cage 10 can include a cavity 60 for bone product placement. The cage 10 includes two built in internalized screw/drill guides 80, 90 (e.g., approximately having a 25 degree angulation), one for each screw 30, 40, which orient the screws 30, 40 bi-directionally in opposite directions. The cage 10 can include a screw guide tunnel exit 13 adjacent to the bone cavity 60 (FIG. 1). One of ordinary skill in the art will recognize that the internalized screw/drill guides 80, 90 can have different degrees of angulation and/or different positions within the cage 10.

In an embodiment, the cage includes at least one screw guide 80 or 82 having a predetermined trajectory (e.g., preferably having a 25 degree angulation) that may make placement of all screws equally facile, more amenable to multi-level placement, and may diminish the need for external drill guides. In other embodiments, the cage includes at least two screw guides 80, 82 having a predetermined trajectory (e.g., preferably having a 25 degree angulation) that may make placement of all screws equally facile, more amenable to multi-level placement, and may diminish the need for external drill guides. In other embodiments, the cage can include a screw guide 80, 82 having another predetermined trajectory, such as an angulation of substantially 25 degrees (e.g., an angulation ranging from 20 degrees to 30 degrees). In other embodiments, the cage can include a screw guide 80, 82 having another predetermined trajectory, such as an angulation ranging from 20 degrees to 25 degrees, an angulation ranging from 25 degrees to 30 degrees, an angulation ranging from 25 degrees to 35 degrees, an angulation ranging from 25 degrees to 35 degrees, an angulation ranging from 20 degrees to 40 degrees, an angulation ranging from 25 degrees to 40 degrees, etc. The embodiments of the cage can include one or more screw/drill guides 80, 82 having different angles and/or different positions within the cage.

The built in tunnels of the screw guides 80, 90 provide an important advantage of ensuring that only one prescribed angled trajectory is possible for transvertebral screw placement. The built in tunnels narrow going downward. This facilitates the locking of the screw head to the top of the cage 10 even in the absence of the locking mechanism described herein. Embodiments of the intervertebral cages 10 can be designed with internalized screw/drill guides 80, 90 with different angles and/or different positions within the cage 10. The angle and size of the screws 30, 40 make them amenable to single or multi-level placement. The superior and inferior surfaces or edges of the lumbar cage 10 can include ridges 50 or the like to facilitate integration and fusion with superior and inferior vertebral bodies.

The embodiment can include a leaf spring 20 which can be, for example, press-fit into the indentation 70 adjacent to the self-drilling internal screw guides, 80, 90 on top of the cage 10. The leaf spring 20 can be manufactured from a variety of materials, such as titanium. When the screws 30, 40 with ratcheted screw heads are turned, the first screw member 30 and the second screw member 40 are locked in a final position by its final turn when the screw head is flush with the surface of the cage 10. The adjacent leaf spring 20 prevents screw back out or pull out by engaging and locking the space between the ratchet teeth (trough) of the screw head when the screws 30, 40 are in their final resting positions. This engagement prevents any rotation of the screw 30, 40 in the opposite direction.

The exemplary embodiments of the locking mechanism are an evolutionary advance and improvement compared to the apparatus illustrated in the aforementioned related applications. The novel embodiments are quite unique and different from all other conventional screw locking mechanisms.

Figure 2A:
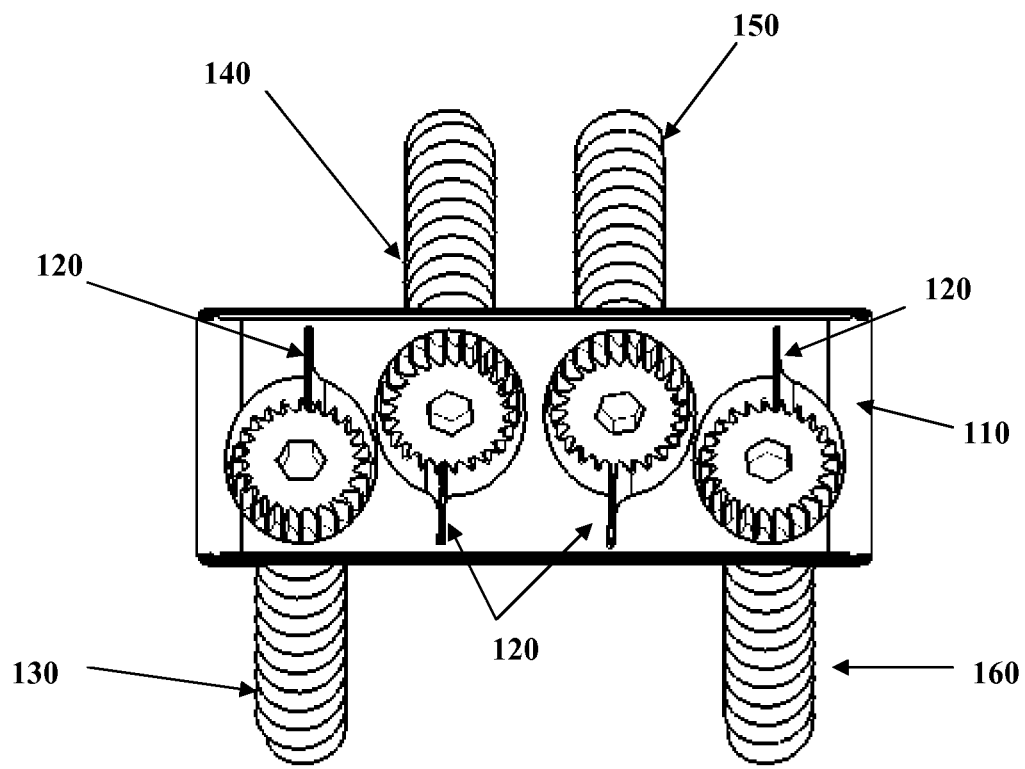
FIG. 2A illustrates a top view of an anterior lumbar intervertebral cage/BDFT screw construct according to an embodiment of the invention.
Figure 2B:
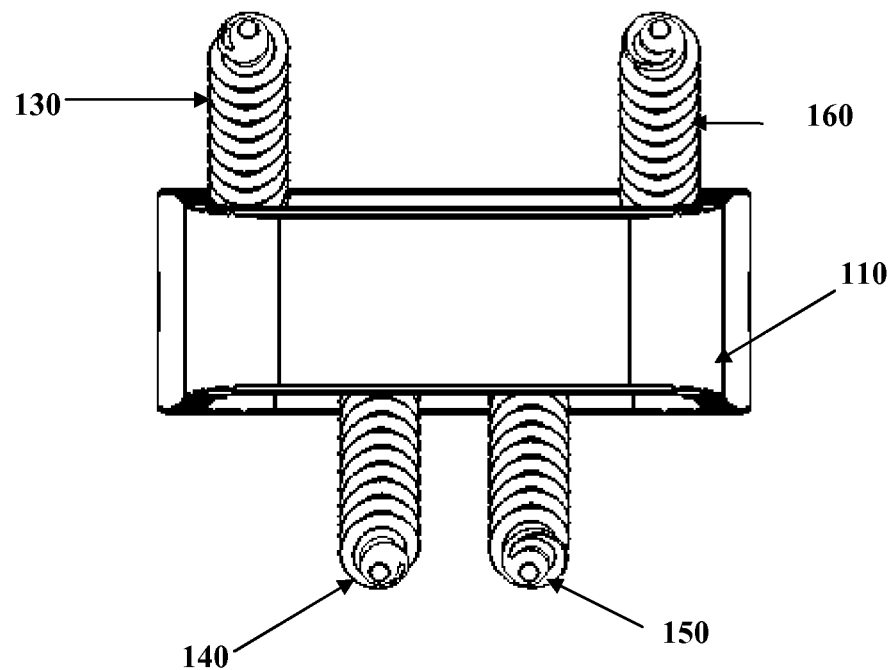
FIG. 2B illustrates a bottom view of an anterior lumbar intervertebral cage/BDFT screw construct according to an embodiment of the invention.
Figure 2C:
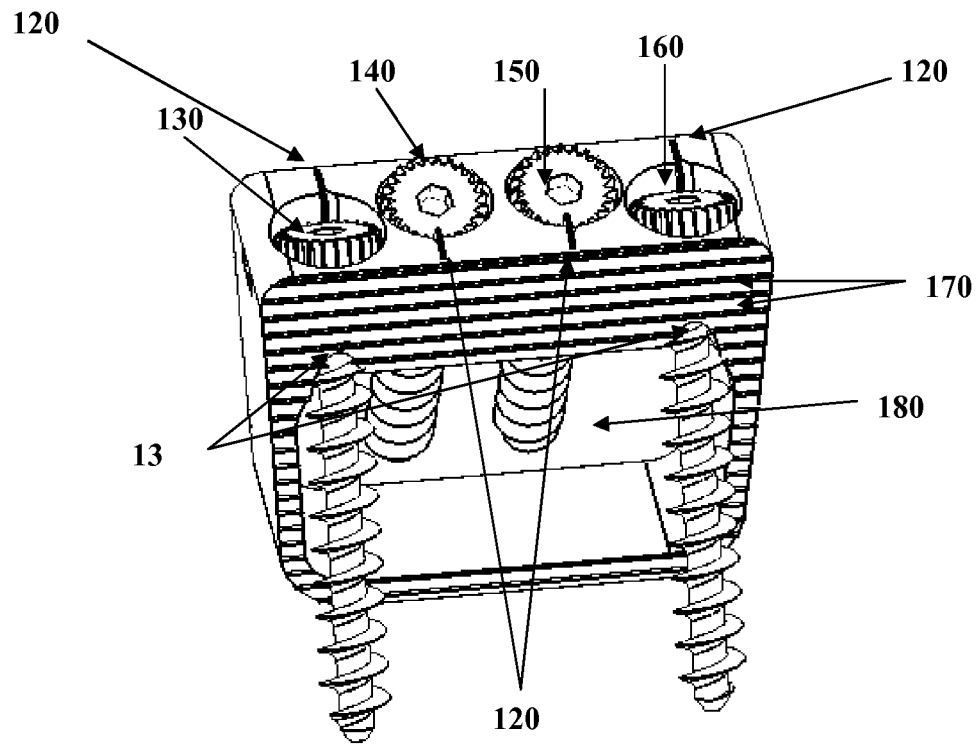
FIG. 2C illustrates a top, perspective view of an anterior lumbar intervertebral cage/BDFT screw construct according to an embodiment of the invention.
Figure 2D:
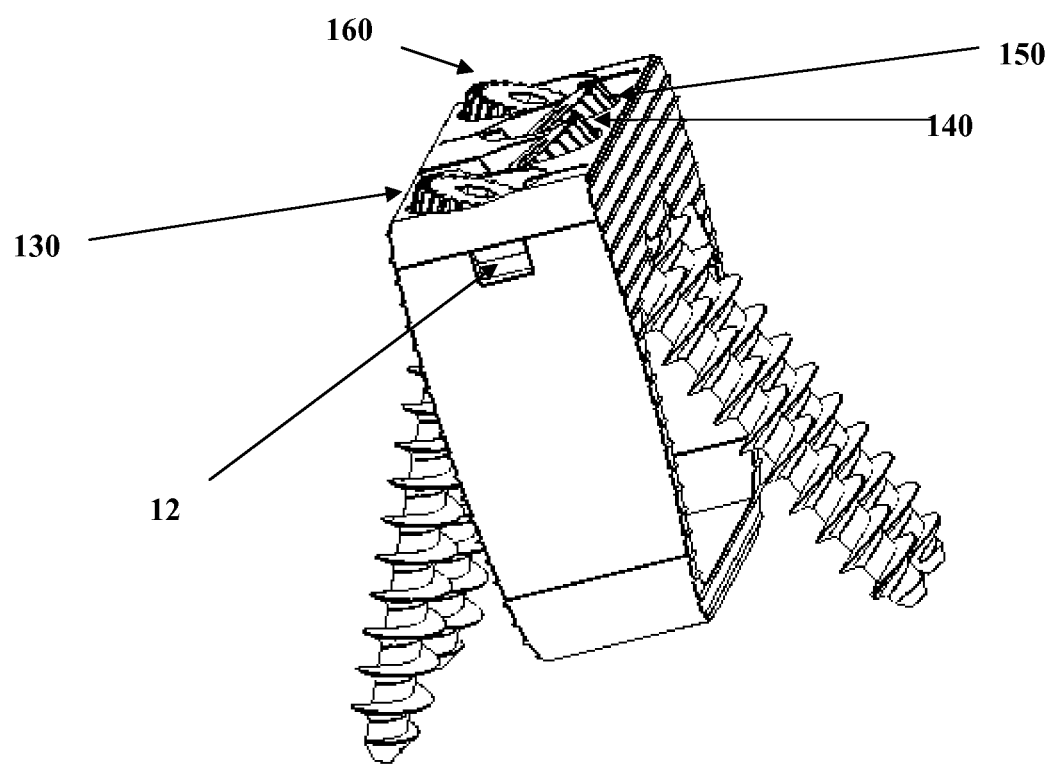
FIG. 2D illustrates a side, perspective view of an anterior lumbar intervertebral cage/BDFT screw construct according to an embodiment of the invention.
Figure 2E:
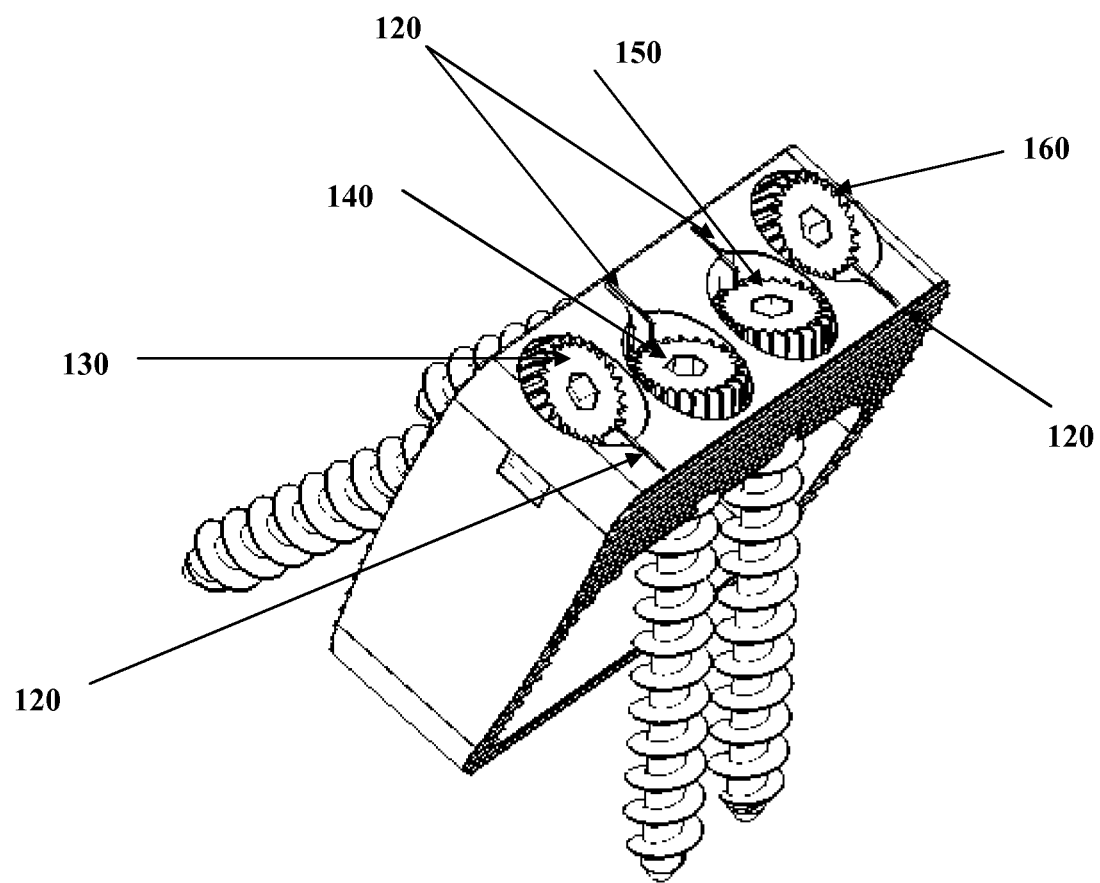
FIG. 2E illustrates a top, perspective view of an anterior lumbar intervertebral cage/BDFT screw construct according to an embodiment of the invention.
Figure 2F:
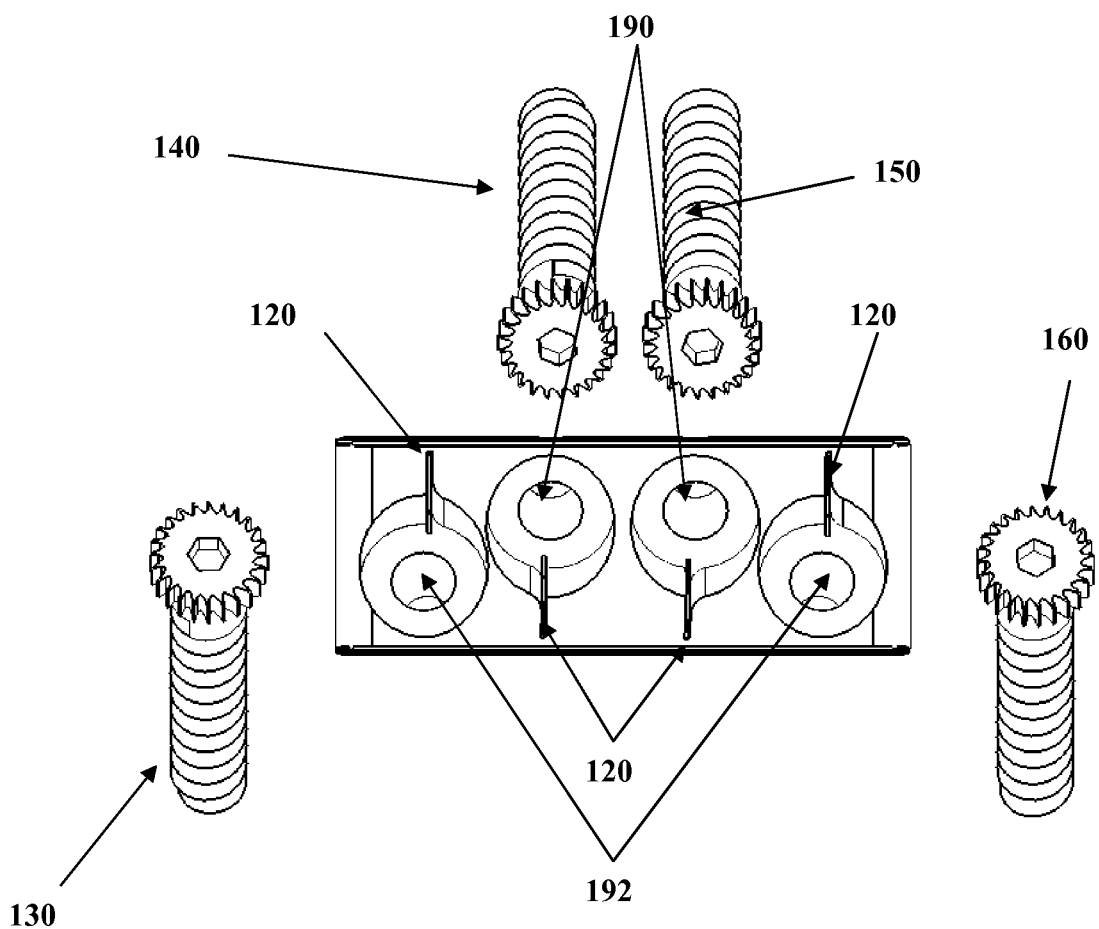
FIG. 2F illustrates a top exploded view of an anterior lumbar intervertebral cage/BDFT screw construct according to an embodiment of the invention.
Figure 2G:
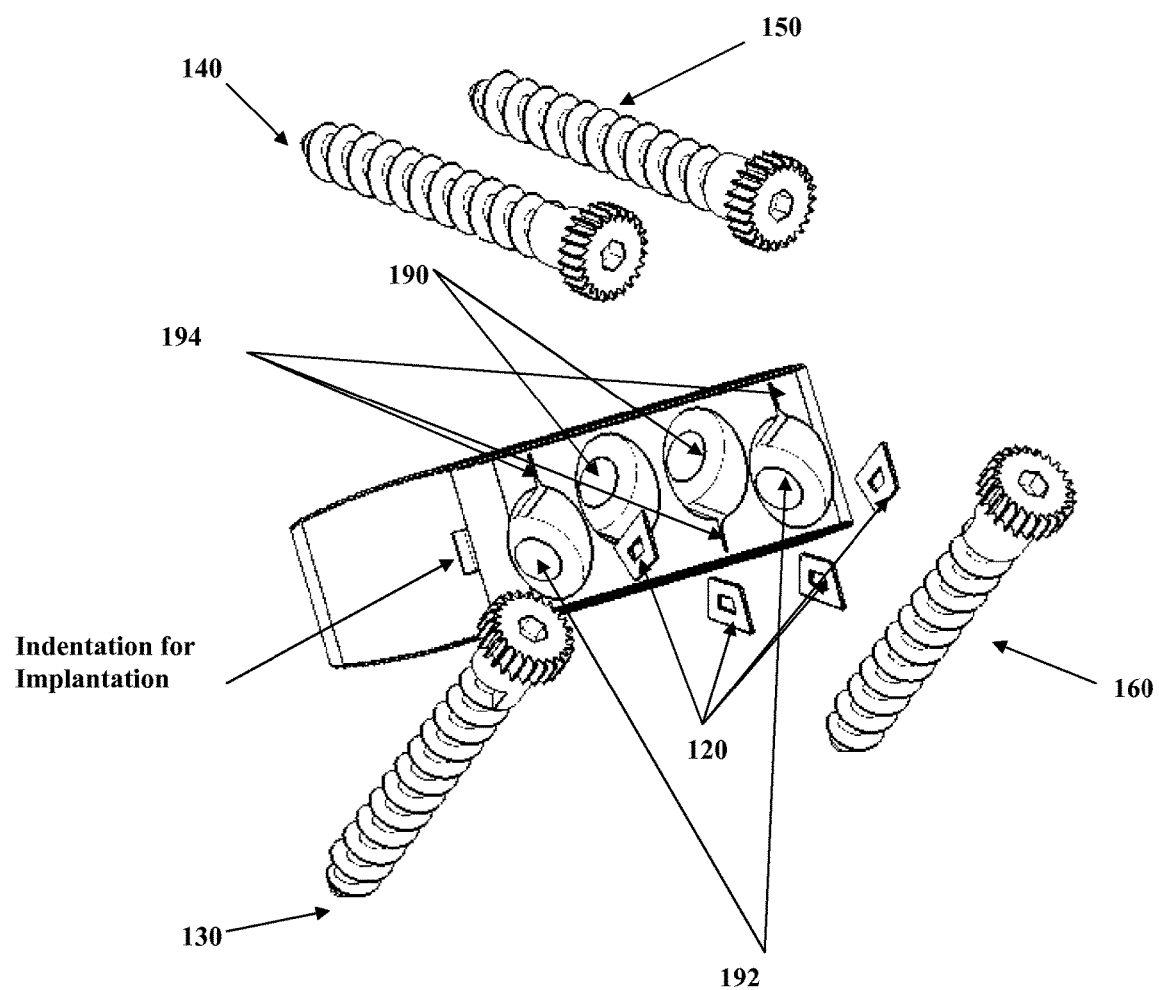
FIG. 2G illustrates a top, perspective exploded view of an anterior lumbar intervertebral cage/BDFT screw construct according to an embodiment of the invention.

FIGS. 2A-2G illustrate three-dimensional views of an exemplary embodiment of an anterior lumbar intervertebral cage/BDFT construct. In this embodiment, the cage 110 includes indentations 194 on top of the cage 10 laterally adjacent to all four internalized screw guides 190, 192 (FIG. 2G), which contain press-fit leaf springs 120. The cage 110 also can include indentations 12 on both side surfaces for insertion of prongs of an implantation tool. This cage 110 can be larger than the cervical cage 10 and also can include elliptically contoured sidewalls when view from the side to fit into the bi-concave lumbar disc space (FIG. 2D). The cage 110 includes four (4) horizontally aligned internalized screw guides 190, 192 for four (4) screws 130, 140, 150, 160. The two lateral (left and right) screws 130, 160 are oriented inferiorly, and the two middle screws 140, 150 are oriented superiorly. The axes of these guides 190, 192 and screws 130, 140, 150, 160 are not perfectly horizontal with respect to each other. Each lateral screw guide/screw is obliquely oriented with respect to its adjacent medial screw guide/screw. This is necessary to achieve the proper trajectory for bone penetration along with the precise angle of the screw guides. The screw guide tunnel exits 13 are illustrated in FIG. 2C and are in continuity (connected) with the enlarged bone cavity 180. In the embodiment, the orientations of the four screw guides 190, 192 (and screws; 130, 140, 150, 160) are selected because of their symmetry and inherent stability.

The cage 110 can include a large cavity 180 for bone product placement. The cage 110 includes four built-in internalized screw/drill guides 190, 192 (e.g., having an approximate 25 degree angulation), one for each screw 130, 140, 150, 160. Other embodiments of the intervertebral cage 110 can be designed with internalized screw/drill guides 190, 192 with different angles and/or different positions within the cage 110. The angle and size of the screws 130, 140, 150, 160 make them amenable to single or multi-level placement. The superior and inferior surfaces or edges of the cage 110 can include ridges 170 or the like to facilitate integration and fusion with superior and inferior vertebral bodies. In an embodiment, there are no compartmental divisions in the cavity 180 for bone product placement to maximize the quantity of bone for fusion.

The cage 110 includes four leaf springs 120 that can be, for example, press-fit to the indentations 194 adjacent to the internalized screw guides 190, 192 on top of the cage 110 (FIG. 2). In the embodiment, the cage 110 includes one leaf spring locking mechanism 120 per screw 130, 140, 150, 160. However, in other embodiments, one locking mechanism 120 can be provided for each screw 130, 140, 150, 160, or one locking mechanism 120 can be provided for two or more screws 130, 140, 150, 160. The top of the cage 110 includes an indentation 194 for each leaf spring locking mechanism 120. Each leaf spring locking mechanism 120 also can be designed to rest and be press-fit into the indentations 194, which are adjacent to the in-built self drilling screw guides 190, 192. The leaf spring locking mechanism 120 can be manufactured from a variety of materials, such as titanium.

When each of the screws 130, 140, 150, 160 with ratcheted screw heads are turned, the screws 130, 140, 150, 160 are locked in a final position by its final turn when the screw head is flush with the surface of the cage 110. The adjacent leaf spring 120 prevents screw back out or pull out by engaging and locking the space between the ratchet teeth of the screw head (trough) when the screws 130, 140, 150, 160 are in their final resting positions. This engagement prevents any rotation of the screw 130, 140, 150, 160 in the opposite direction. It should also be noted that because of the narrowing of the screw guide tunnel 190, 192, when the screw head is countersunk into the top of the cage 110, this also serves as a preliminary locking mechanism.

The exemplary embodiments are an evolutionary advance and improvement compared to the apparatus illustrated in the aforementioned related applications, and are quite unique and different from all other conventional locking mechanisms used for other types of anterior lumbar cages.

A possible conventional device conceivably may include anterior placed lumbar implants with perforating screws. The conventional device may include a horseshoe implant having a plurality of cylindrical holes with smooth inner surfaces and comprise only one stop for the heads of the bone screws to be inserted into them. The placement of five cylindrical holes is oriented within the cage in a non-symmetric manner.

In comparison, the exemplary embodiments differ in many substantial ways from the conventional devices. For example, the exemplary embodiments provide a symmetric orientation of the screw holes, as well as a screw locking mechanism. The exemplary embodiments also provide an angulation/trajectory (e.g., an approximate twenty five degree angulation/trajectory) for preventing pull-out or back-out of the screws that would make placement of all screws in a manner which would lead to maximum stability of the construct within the vertebral space, and obviate the need for external drill guides, and surgeon trajectory angulation guess work.

In another possible conventional device, multiple embodiments of lumbar intervertebral implants may be presented which include one with internally threaded bore holes, another embodiment with a front plate mounted at the front surface of the implant, and another embodiment with the front place displaceably configured to move vertically relative to the implant. In addition, the disclosed preferred borehole axes may be 35-55 degrees. These conventional devices may have four screw perforations that are not aligned four in a row. Two of the screw holes may be laterally placed on the left, one on top of each other, the top one with a superior trajectory, and the bottom with an inferior trajectory. Likewise, two perforations may be placed on the right, one on top of each other, the top one with a superior trajectory and the bottom one with an inferior trajectory. The disclosed screw locking mechanism may be a screw with an external thread matching the internal borehole thread, or spiral springs.

In comparison, the anterior lumbar construct of the exemplary embodiments differs in many substantial ways from these conventional devices. The exemplary embodiments include a single cage construct with four (4) internalized drill guides arranged horizontally in a row. The lateral screw guides/screws are obliquely oriented with the respect to their adjacent medial screw guides/screws. The middle two screws are oriented superiorly, and the lateral left and right screws are oriented inferiorly. This symmetric alignment of screws and orientations within the superior and inferior vertebral bodies (e.g., two middle superiorly projecting screws, and two laterally projecting inferior screws) make the fixation to the superior and inferior vertebral bodies much more symmetric and thus more stable preventing subsidence. In an exemplary embodiment, the cage includes a screw guide having a predetermined trajectory (e.g., an approximate trajectory of 25 degrees or another angulation) that makes placement of all screws equally facile, more amenable to multi-level placement, and diminishes the need for external drill guides. Furthermore, the exemplary screw locking mechanism, which is press-fit to the cage, is unique and differs substantially from the conventional approach of matching screw/cage threads or spiral springs.

Figure 3A:
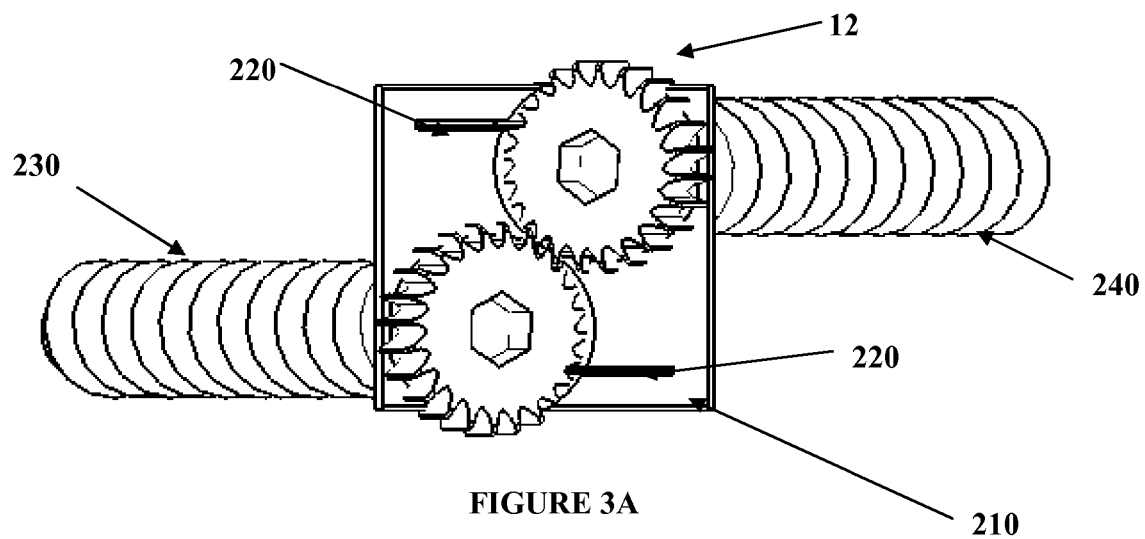
FIG. 3A illustrates a top view of a posterior lumbar rectangularly designed intervertebral cage/BDFT construct according to an embodiment of the invention.
Figure 3B:
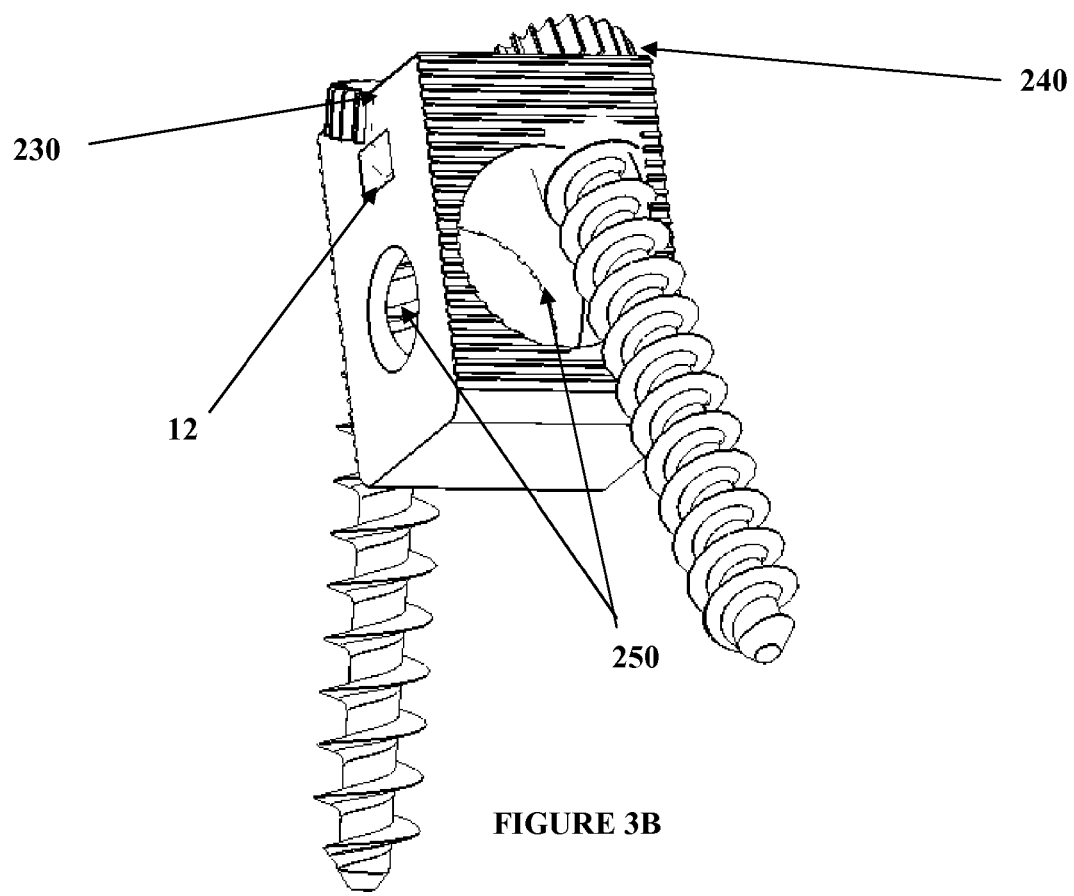
FIG. 3B illustrates a front, perspective view of a posterior lumbar rectangularly designed intervertebral cage/BDFT construct according to an embodiment of the invention.
Figure 3C:
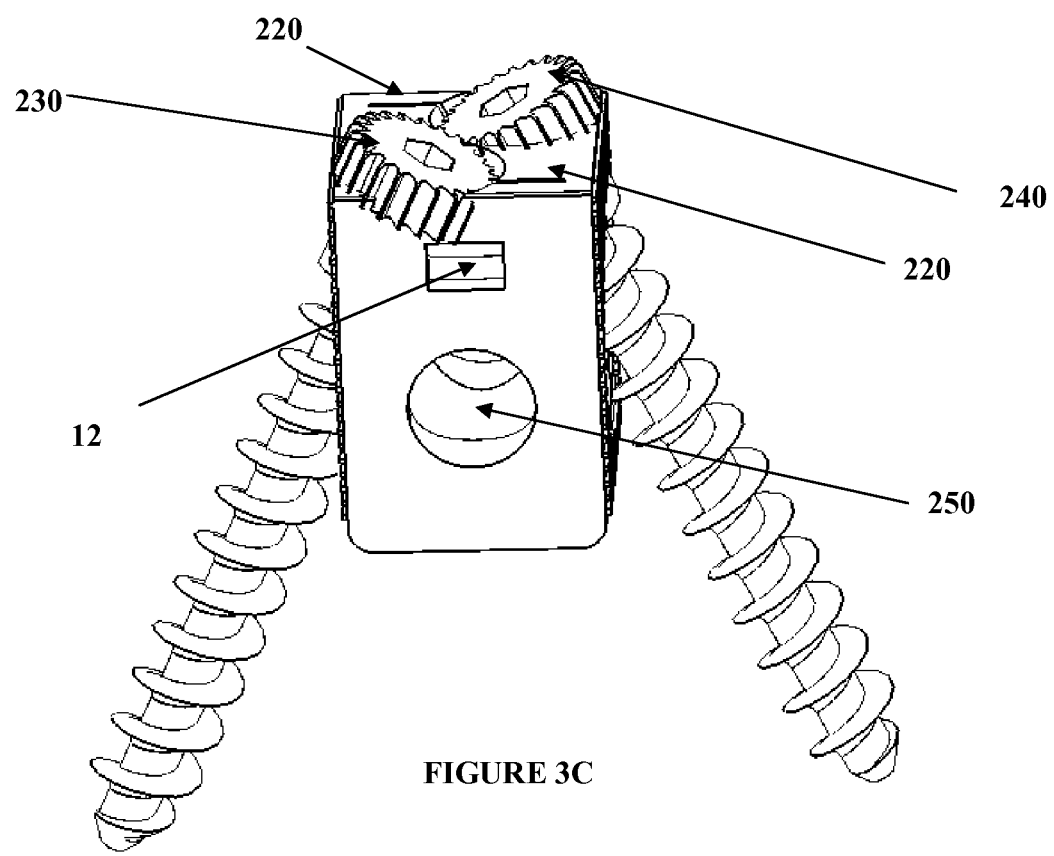
FIG. 3C illustrates a side, perspective view of a posterior lumbar rectangularly designed intervertebral cage/BDFT construct according to an embodiment of the invention.
Figure 3D:
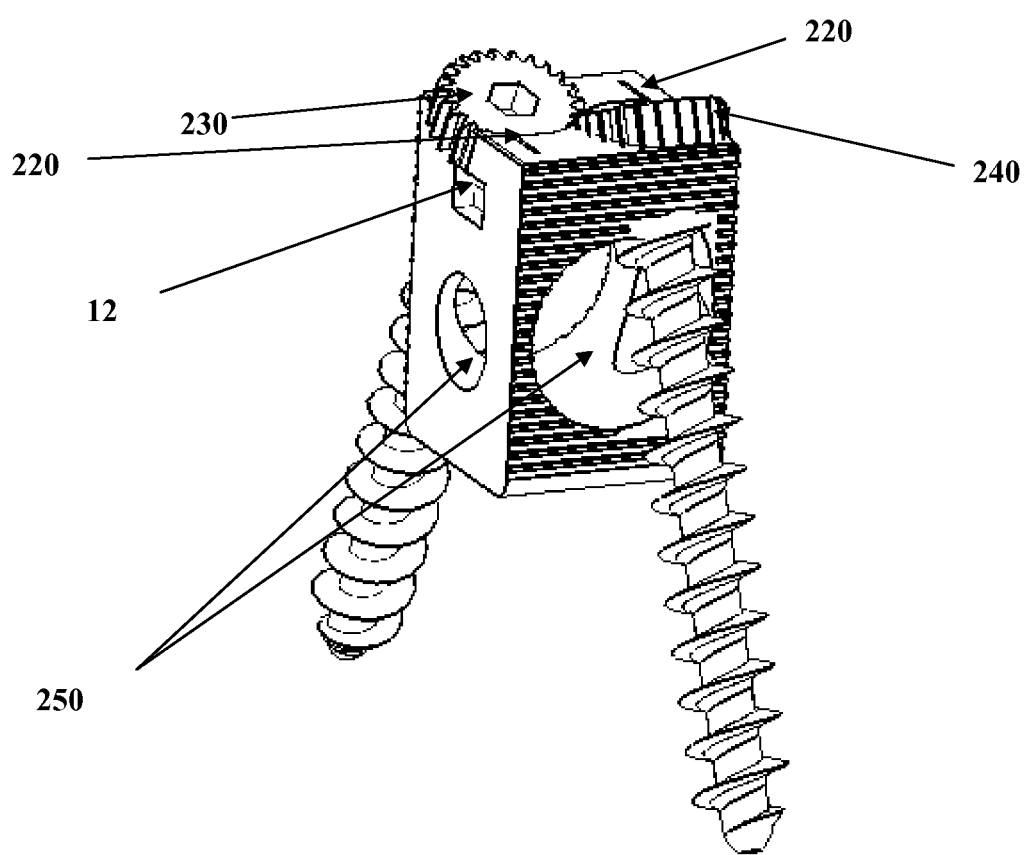
FIG. 3D illustrates a front, perspective view of a posterior lumbar rectangularly designed intervertebral cage/BDFT construct according to an embodiment of the invention.
Figure 3E:
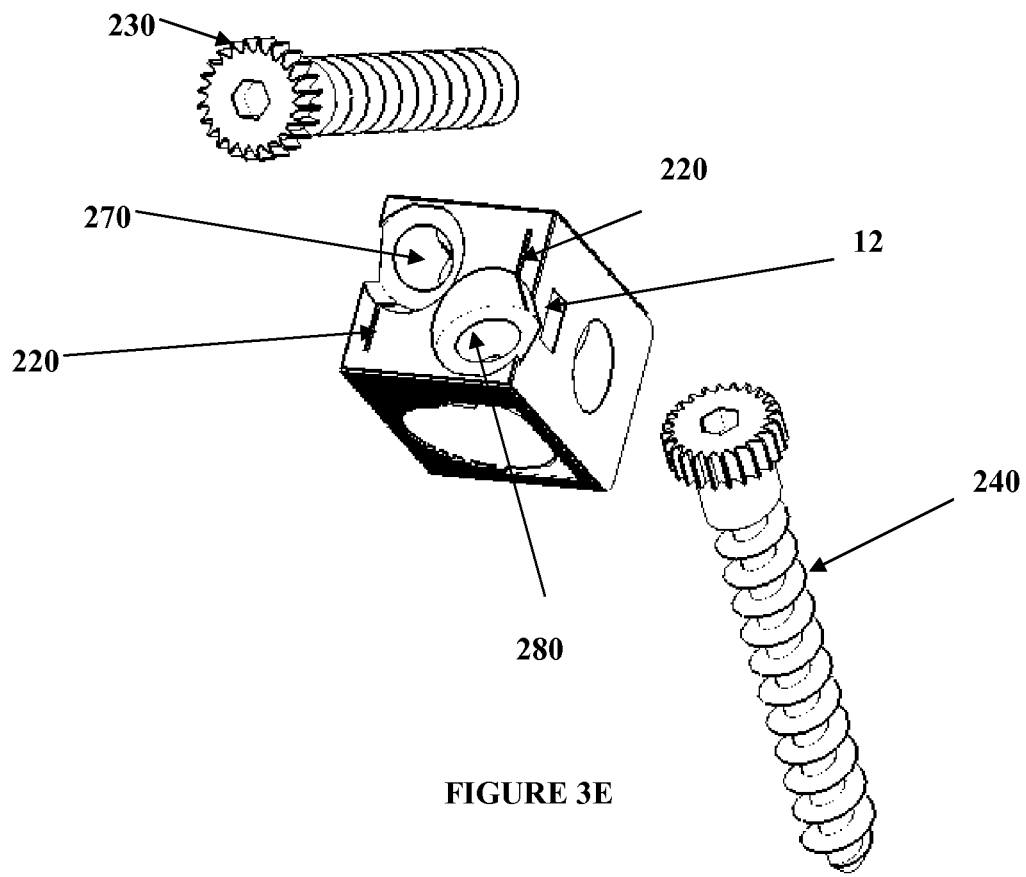
FIG. 3E illustrates a top, perspective exploded view of a posterior lumbar rectangularly designed intervertebral cage/BDFT construct according to an embodiment of the invention.
Figure 3F:
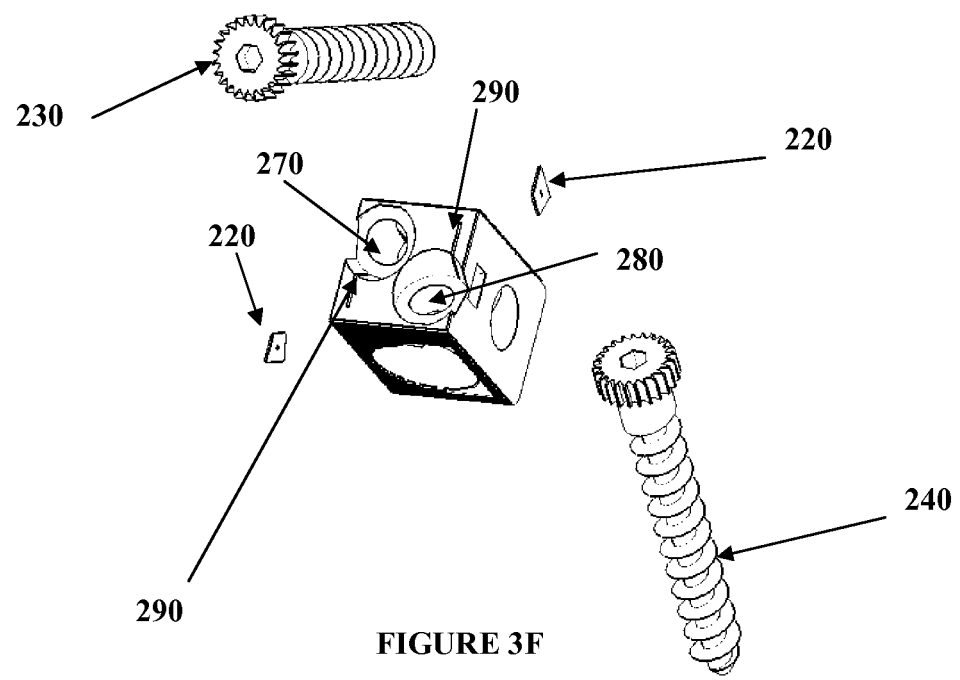
FIG. 3F illustrates a top, perspective exploded view of a posterior lumbar rectangularly designed intervertebral cage/BDFT construct according to an embodiment of the invention.

FIGS. 3A-3F illustrate three-dimensional views of an exemplary embodiment of a posterior lumbar rectangular intervertebral cage/BDFT construct. In this embodiment, the cage 210 includes indentations 290 on top of the cage 290 that are adjacent to the internal screw guides 270, 280 (FIG. 3F). The indentations 290 contain press-fit leaf springs 220. The cage 210 also includes indentations 12 on both side surfaces of the construct for the prong placement of an implantation tool. The screws 230, 240 perforate and orient in opposing superior and inferior directions.

The cage 210 can include a cavity 250 for bone product placement. The top and bottom portions of the rectangular cage 210 are elliptically contoured to naturally fit into the bi-concave intervertebral disc space (FIG. 3C; side view). The top of cage 210 is a square with equal width and length. The cage 210 includes built-in internalized screw/drill guides 270, 280 having a predetermined angled trajectory (e.g., having an approximate 25 degree angulation), and their axes are not horizontal, but oblique one to the other and very close to each other. Each screw guide/screw 270, 280 occupies one corner of a square, obliquely oriented one to the other (FIG. 3A). This necessary to achieve proper screw penetration in so narrow a posterior lumbar interspace. One of the guides is angled rostrally (superiorly) (e.g., guide 270) and the other caudally (inferiorly) (e.g., guide 280). The intervertebral cages 210 can be designed with internalized screw/drill guides 270, 280 with different angles and/or different positions within the cage 210. Because the tunnel of the screw guide 270, 280 narrows, when the screw 230, 240 is countersunk on top of the cage 210, the screw 230, 240 is preliminarily locked, even in the absence of this locking mechanism. The angle and size of the screws 230, 240 make them amenable to single or multi-level placement. The screw guide exit tunnel 13 adjacent to the bone cavity 250 is illustrated in FIG. 3D. The superior and inferior surfaces or edges can include ridges or the like to facilitate integration and fusion with superior and inferior vertebral bodies. One of these constructs is placed posteriorly into the intervertebral space on the left side, and the other on the right side.

The cage 210 includes a leaf spring screw locking mechanism 220 that can be, for example, press-fit into the indentation 290 adjacent to the internalized screw guides 270, 280 on top of the cage 210. The top of the cage 210 can have an indentation 290 to engage the spring leaf locking mechanism 220. The spring leaf locking mechanism 220 can be manufactured from a variety of materials, such as titanium. When the screws 230, 240 with ratcheted screw heads are turned, the first screw member 230 and the second screw member 240 are locked in a final position by its final turn when the screw head is flush with the surface of the cage 210. The adjacent leaf spring 20 prevents screw back out or pull out by engaging and locking the space between the ratchet teeth (trough) of the screw head when the screws 230, 240 are in their final resting positions. This engagement prevents any rotation of the screw 230, 240 in the opposite direction.

The exemplary embodiment of this novel intervertebral cage 210 is an evolutionary advance and improvement compared to the apparatus illustrated in the aforementioned related applications. The novel cage 210 also is quite unique and different from other conventional locking mechanisms used for other known cervical and lumbar anterior or posterior plate screws. No other conventional posterior lumbar intervertebral cage BDFT/screw constructs are known.

Figure 4A:
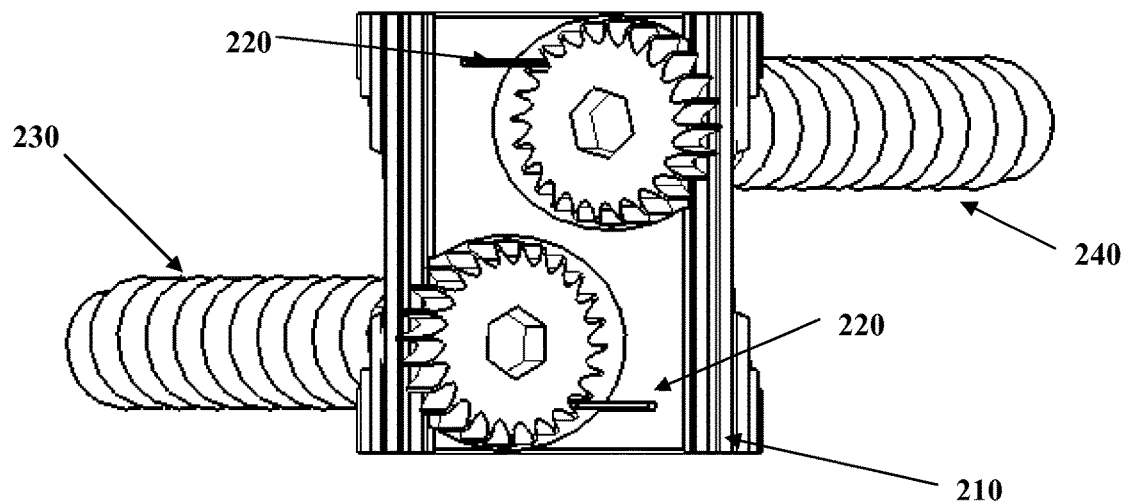
FIG. 4A illustrates a top view of a posterior lumbar elliptically designed intervertebral cage/BDFT construct according to an embodiment of the invention.
Figure 4B:
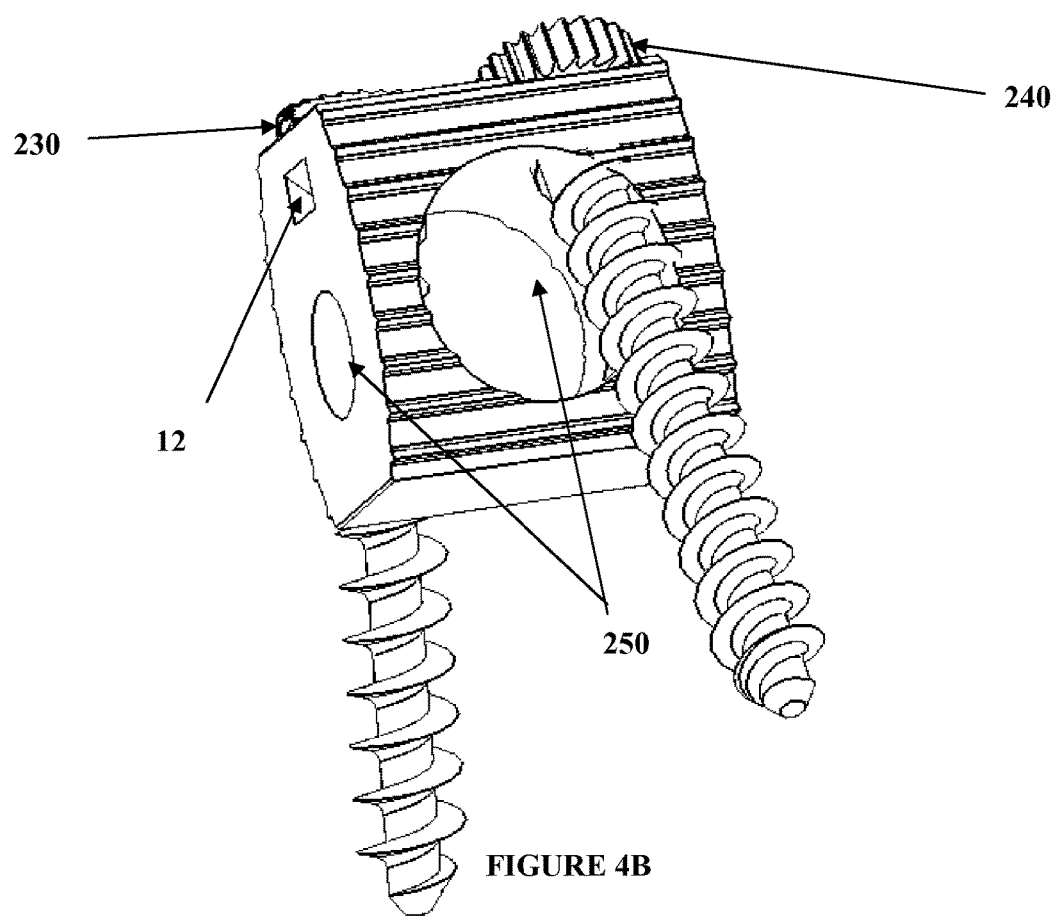
FIG. 4B illustrates a front, perspective view of a posterior lumbar elliptically designed intervertebral cage/BDFT construct according to an embodiment of the invention.
Figure 4C:
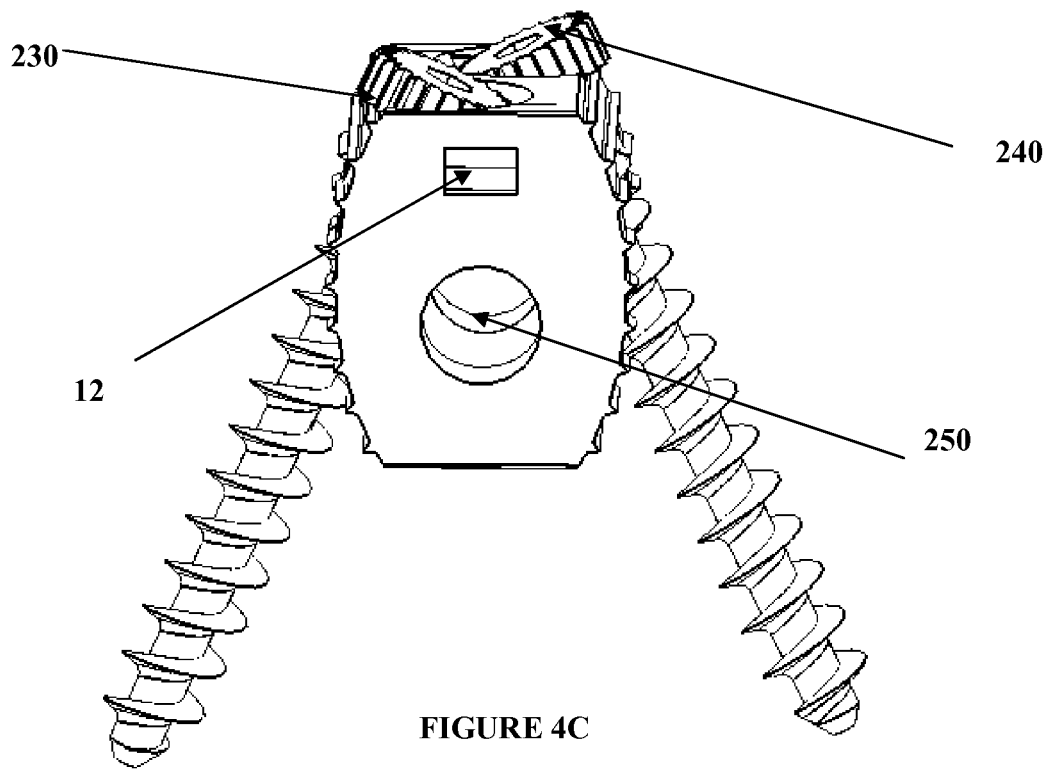
FIG. 4C illustrates a side view of a posterior lumbar elliptically designed intervertebral cage/BDFT construct according to an embodiment of the invention.
Figure 4D:
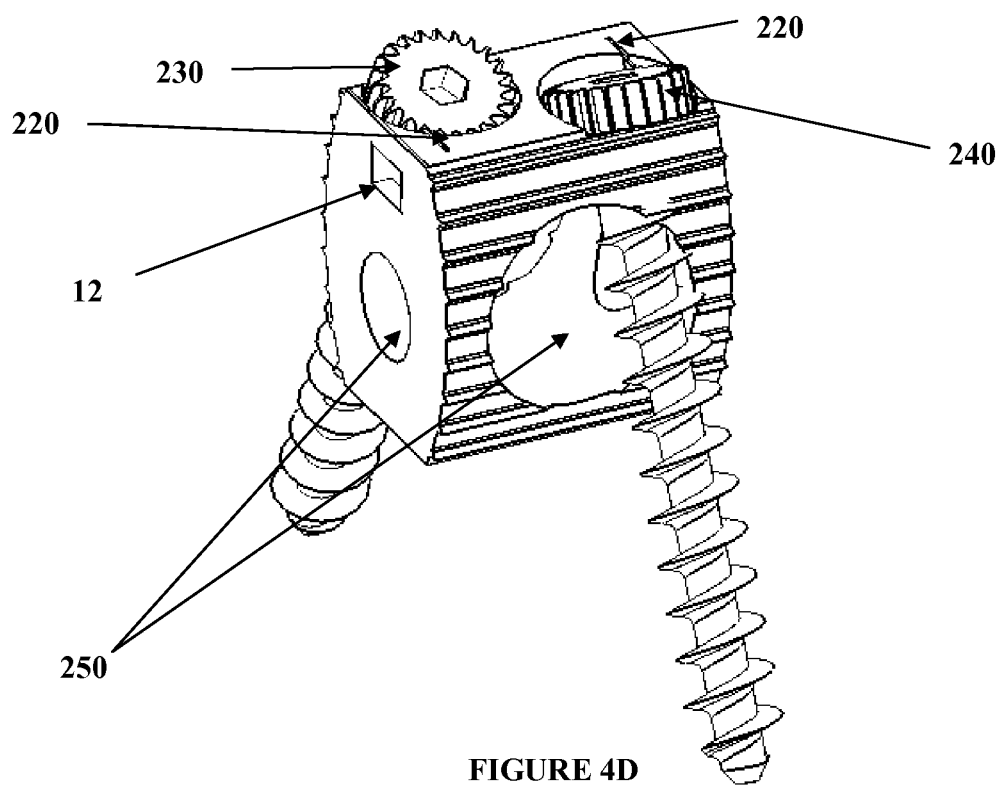
FIG. 4D illustrates a front, perspective view of a posterior lumbar elliptically designed intervertebral cage/BDFT construct according to an embodiment of the invention.
Figure 4E:
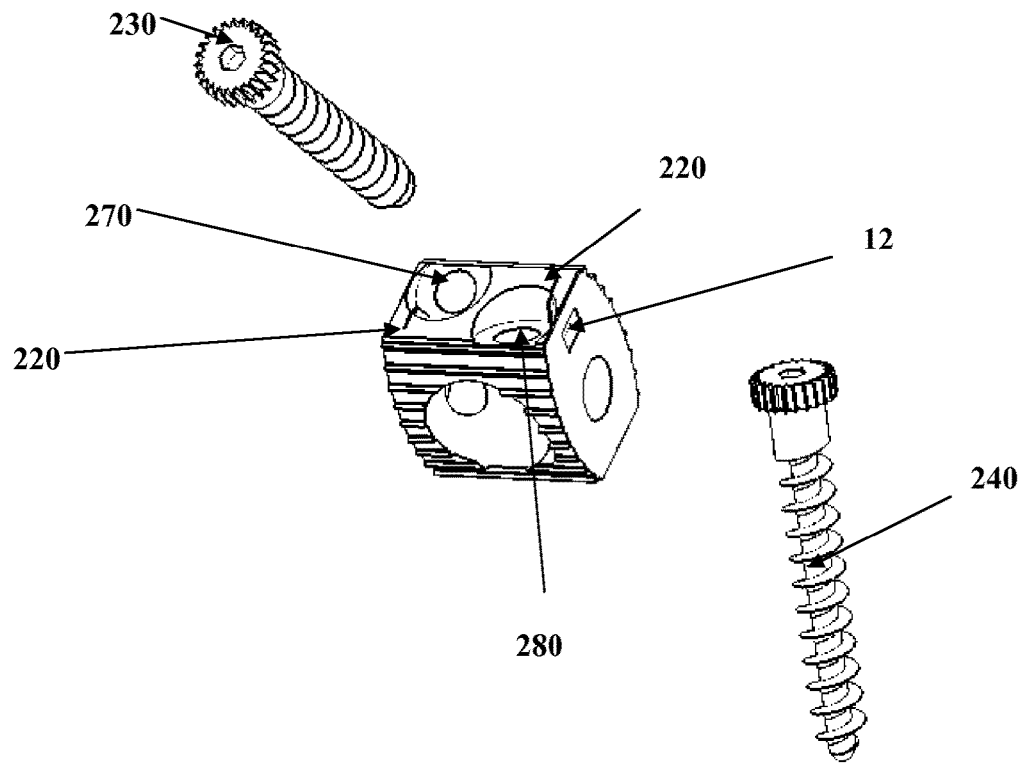
FIG. 4E illustrates a top, perspective exploded view of a posterior lumbar elliptically designed intervertebral cage/BDFT construct according to an embodiment of the invention.
Figure 4F:
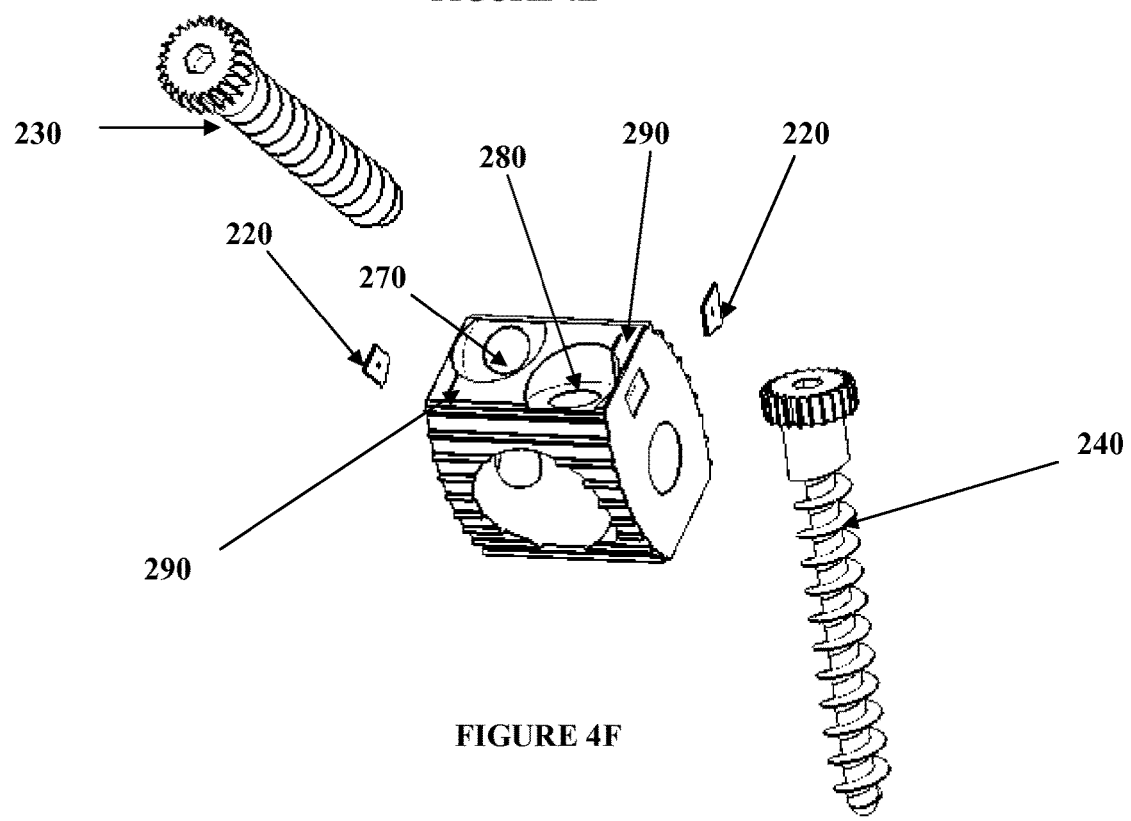
FIG. 4F illustrates a top, perspective exploded view of a posterior lumbar elliptically designed intervertebral cage/BDFT construct according to an embodiment of the invention.

FIGS. 4A-4F illustrate three-dimensional views of an exemplary embodiment of a posterior lumbar elliptical intervertebral cage/BDFT construct. In this embodiment, indentations 290 on top of the cage 210 are adjacent to the internal screw guides 270, 280 (FIG. 4F). The indentations 290 can contain press-fit leaf springs, 220.

The cage 210 also can include indentations or slots 12 on both side surfaces of the cage 210 for insertion of a prong of an implantation tool (see example cage and tool in FIG. 5D; the cage 210 can engage the tool in a similar manner), and more particularly, that engage the distal medial oriented male protuberance of a lateral griper prong of an implantation tool.

The screws 230, 240 perforate and orient in opposing superior and inferior directions. The cage 210 can include a cavity 250 for bone product placement. The entire body of this cage 210 can be elliptical as opposed to the top and bottom portions of the rectangular cage of the previous embodiment 210, and can be contoured when viewed from the side to naturally fit into the bi-concave intervertebral disc space (FIG. 4C).

The cage 210 includes built-in internalized screw/drill guides 270, 280 having a predetermined angled trajectory (e.g., having an approximate 25 degree angulation), and their axes are not horizontal, but oblique one to the other and very close to each other. Each screw guide/screw occupies one corner of a square, obliquely oriented one to the other (FIG. 4A). This necessary to achieve proper screw penetration in so narrow a posterior lumbar interspace. One of the guides is angled rostrally (superiorly) (e.g., guide 270) and the other caudally (inferiorly) (e.g., guide 280). The intervertebral cages 210 can be designed with internalized screw/ drill guides 270, 280 with different angles and/or different positions within the cage 210. Because the tunnel of the screw guide 270, 280 narrows, when the screw 230, 240 is countersunk on top of the cage 210, the screw 230, 240 is preliminarily locked, even in the absence of this locking mechanism. The angle and size of the screws 230, 240 make them amenable to single or multi-level placement. The screw guide exit tunnel 13 adjacent to the bone cavity 250 is illustrated in FIG. 4D. The superior and inferior surfaces or edges can include ridges or the like to facilitate integration and fusion with superior and inferior vertebral bodies. One of these constructs is placed posteriorly into the intervertebral space on the left side, and the other on the right side.

The cage 210 includes a leaf spring screw locking mechanism 220 that can be, for example, press-fit into the indentation 290 adjacent to the internalized screw guides 270, 280 on top of the cage 210. The top of the cage 210 can have an indentation 290 to engage the spring leaf locking mechanism 220. The spring leaf locking mechanism 220 can be manufactured from a variety of materials, such as titanium. When the screws 230, 240 with ratcheted screw heads are turned, the first screw member 230 and the second screw member 240 are locked in a final position by its final turn when the screw head is flush with the surface of the cage 210. The adjacent leaf spring 220 prevents screw back out or pull out by engaging and locking the space between the ratchet teeth (trough) of the screw head when the screws 230, 240 are in their final resting positions. This engagement prevents any rotation of the screw in the opposite direction.

The exemplary embodiment of this novel intervertebral cage 210 is an evolutionary advance and improvement compared to the apparatus illustrated in the aforementioned related applications. The novel cage 210 also is quite unique and different from other conventional locking mechanisms used for other known cervical and lumbar anterior or posterior plate screws. No other conventional posterior lumbar intervertebral cage BDFT/screw constructs are known.

2. Exemplary Surgical Method

Exemplary surgical steps for practicing one or more of the forgoing embodiments will now be described.

Anterior cervical spine placement of the intervertebral cage/BDFT screw construct 10 (FIG. 1) can be implanted via previously described techniques for anterior cervical discectomy and fusion. Some but not all of these techniques include, open, microscopic, closed endoscopic or tubular. Fluoroscopic or any other form of visualized guidance can be used for this procedure.

After the adequate induction of anesthesia the patient is placed in a supine position. An incision is made overlying the intended disc space or spaces, and the anterior spine is exposed. A discectomy is performed and the endplates exposed. The disc height is measured and an anterior cervical intervertebral cage of the appropriate disc height, width and depth is selected. The central cavity is packed with bone fusion material, autologous bone graft, allograft, alone or in combination with any commercially available bone fusion promoting product. The cage 10 is then inserted into the midline of the anterior disc space routinely until it is flush or countersunk relative to the vertebral body above and below. The BDFT screws 30, 40 are then inserted into the internalized rostrally (superiorly) and caudally (inferiorly) angled screw guides 80, 90. A drill with or without a drill guide can be used to prepare for screw placement. This is not absolutely necessary. Because the cage 10 has internalized screw guides 80, 90, self-drilling/self-tapping screws 30, 40 of the appropriately selected lengths can be directly screwed into the vertebral bodies once placed into the internalized drill-guided angled tunnels. The cage's screw guides 80, 90, which have internalized tunnels, direct the screws 30, 40 into the superior and inferior vertebral bodies in the predetermined angle of the internalized tunnels. There is no other angled trajectory other than that which is built into the internalized screw guide/tunnel of the cage 10 that the screw 30, 40 can be oriented in. Hence, there is no absolute need for fluoroscopic guidance.

Once the surgeon is satisfied with the position and placement of the cage 10, the BDFT screws 30, 40 can then be locked into their final positions. When each of the BDFT screws 30, 40 with ratcheted screw heads are turned, they penetrate and engage the bone until they are locked in a final position by its final turn when the screw head is flush with the surface of the cage 10. The adjacent leaf spring 20 prevents screw back out or pull out by engaging and locking the space between the ratchet teeth of the screw head (trough) when the screws 30, 40 are in their final resting positions. This engagement because of the geometric arrangement of the ratchet teeth and troughs prevents any rotation of the screw 30, 40 in the opposite direction. Once the screw 30, 40 is in this position it can no longer be backed out without destroying the leaf spring mechanism 20. The surgeon has the option to verify the trajectory fluoroscopically by applying preliminary non-ratcheted BDFT screws 30, 40 which lack ratchet teeth on their screw heads. Once the surgeon is confident of the screw trajectory verified by x-ray, the BDFT screws 30, 40 with screw head ratchet teeth can be inserted and locked in their final position. Because of the presence of internalized screw-guides 80, 90 within the cage 10, this step is not absolutely necessary, but is an option available for the surgeon as a double-check measure.

Anterior or anteriolateral placement of thoracic or lumbar spine intervertebral cage/BDFT screw constructs 110 (FIG. 2) can be implanted via previously described surgical techniques for anterior lumbar discectomy, and transthoracic, anterior-lateral thoracic discectomy. Some but not all of these techniques include, open, microscopic, closed endoscopic or tubular. Fluoroscopic or any other form of visualized guidance can be used for this procedure.

After the adequate induction of anesthesia and after the anterior spine is exposed a discectomy is performed and the endplates exposed. The disc height is measured and an anterior lumbar (or thoracic) intervertebral cage of the appropriate disc height, width and depth is selected. The central cavity 180 is packed with bone fusion material, autologous bone graft, allograft, alone or in combination with any commercially available bone fusion promoting product. The cage 110 is then inserted into the midline of the anterior disc space routinely until it is flush or countersunk relative to the vertebral body above and below. The four BDFT screws 130, 140, 150, 160 with screw heads with ratchet teeth are then inserted into the two middle internalized rostrally (superiorly) and two lateral, caudally (inferiorly) angled screw guides 190, 192. A drill with or without a drill guide can be used to prepare for screw placement. This is not absolutely necessary. Because the cage 110 has internalized screw guides 190, 192, self-drilling/self-tapping screws 130, 140, 150, 160 of the appropriately selected lengths can be directly screwed into the vertebral bodies once placed into the internalized drill-guided angled tunnels. The cage's internalized guides 190, 192, which have internalized tunnels, direct the screws 130, 140, 150, 160 into the superior and inferior vertebral bodies in the predetermined angle of the internalized tunnels. There is no other angled trajectory other than that which is built into the internalized screw guide/tunnel of the cage 110 that the screw 130, 140, 150, 160 can be oriented in. Hence there is no absolute need for fluoroscopic guidance.

Once the surgeon is satisfied with the position and placement of the cage 110, the BDFT screws 130, 140, 150, 160 can then be locked into their final positions. When each of the BDFT screws 130, 140, 150, 160 with ratcheted screw heads are turned, the screws 130, 140, 150, 160 penetrate and engage the bone until they are locked in a final position by its final turn when the screw head is flush with the surface of the cage 110. The adjacent leaf spring 120 prevents screw back out or pull out by engaging and locking the space between the ratchet teeth of the screw head (trough) when the screws 130, 140, 150, 160 are in their final resting positions. This engagement prevents any rotation of the screw 130, 140, 150, 160 in the opposite direction. Once the screw 130, 140, 150, 160 is in this position it can no longer be backed out without destroying the leaf spring mechanism 20. The surgeon has the option to verify the trajectory fluoroscopically by applying preliminary non-ratcheted BDFT screws 130, 140, 150, 160 which lack ratchet teeth on their screw heads. Once the surgeon is confident of the screw trajectory verified by x-ray, the BDFT screws 130, 140, 150, 160 with screw head ratchet teeth can be inserted and locked in their final position. Because of the presence of internalized screw-guides 180, 190 within the cage 110, this step is not absolutely necessary, but is an option available for the surgeon as a double-check measure.

Implantation of the posterior lumbar intervertebral cage/BDFT screw constructs 110 (FIGS. 3 and 4) can be performed via previously described posterior lumbar interbody fusion (PLIF) or posterior transforaminal lumbar interbody fusion (TLIF) procedures. The procedures can be performed open, microscopic, closed tubular or endoscopic techniques. Fluoroscopic guidance can be used with any of these procedures.

After the adequate induction of anesthesia, the patient is placed in the prone position. A midline incision is made for a PLIF procedure, and one or two parallel paramedian incisions or a midline incision is made for the TLIF procedure. For the PLIF procedure, a unilateral or bilateral facet sparing hemi-laminotomy is created to introduce the posterior lumbar construct into the disc space after a discectomy is performed and the space adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

The disc height is measured and a posterior lumbar intervertebral cage/BDFT screw construct (FIGS. 3 and 4) of the appropriate disc height, width and depth is selected. The central cavity 250 is packed with bone fusion material, autologous bone graft, allograft, alone or in combination with any commercially available bone fusion promoting product. Then one construct 210 is placed on either right or left sides, or one construct each is placed into left and right sides. The constructs are inserted such they are flush or countersunk relative to the superior and inferior vertebral bodies. In addition to the central cavities 250 that are packed with bone product, the intervertebral space in between the constructs can also be packed with bone product for fusion.

The BDFT screws 230, 240 are then inserted into internalized rostrally (superiorly) and caudally (inferiorly) angled screw guides 270, 280. A drill with or without a drill guide can be used to prepare for screw placement. This is not absolutely necessary. Because the cage 210 has internalized screw guides 270, 280, self-drilling/self-tapping screws 230, 240 of the appropriately selected lengths can be directly screwed into the vertebral bodies once placed into the internalized drill-guided angled tunnels. The cage's internalized guides 270, 280, which have internalized tunnels, direct the screws 230, 240 into the superior and inferior vertebral bodies in the predetermined angle of the internalized tunnels. There is no other angled trajectory other than that which is built into the internalized screw guide/tunnel 270, 280 of the cage 210 that the screw 230, 240 can be oriented in. Hence, unlike posterior placement of pedicle screws 230, 240 there is no absolute need for fluoroscopic or expensive and cumbersome, frameless stereotactic CT guidance.

Once the surgeon is satisfied with the position and placement of the cage 210, the BDFT screws 230, 240 can then be locked into their final positions. When each of the BDFT screws 230, 240 with ratcheted screw heads are turned, they penetrate and engage the bone until they are locked in a final position by its final turn when the screw head is flush with the surface of the cage 210. The adjacent leaf spring 220 prevents screw back out or pull out by engaging and locking the space between the ratchet teeth of the screw head (trough) when the screws 230, 240 are in their final resting positions. This engagement prevents any rotation of the screw 230, 240 in the opposite direction. Once the screw 230, 240 is in this position it can no longer be backed out without destroying/disrupting the leaf spring mechanism 220. The surgeon has the option to verify the trajectory fluoroscopically by applying preliminary non-ratcheted BDFT screws 230, 240 which lack ratchet teeth on their screw heads. Once the surgeon is confident of the screw trajectory verified by x-ray, the BDFT screws 230, 240 with screw head ratchet teeth can be inserted and locked in their final position. Because of the presence of internalized screw-guides 270, 280 within the cage 210, this step is not absolutely necessary, but is an option available for the surgeon as a double-check measure.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These inventions could replace much pedicle screw, and anterior plating based instrumentation in many but not all degenerative spine conditions.

The speed and simplicity of placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

Figure 5A:
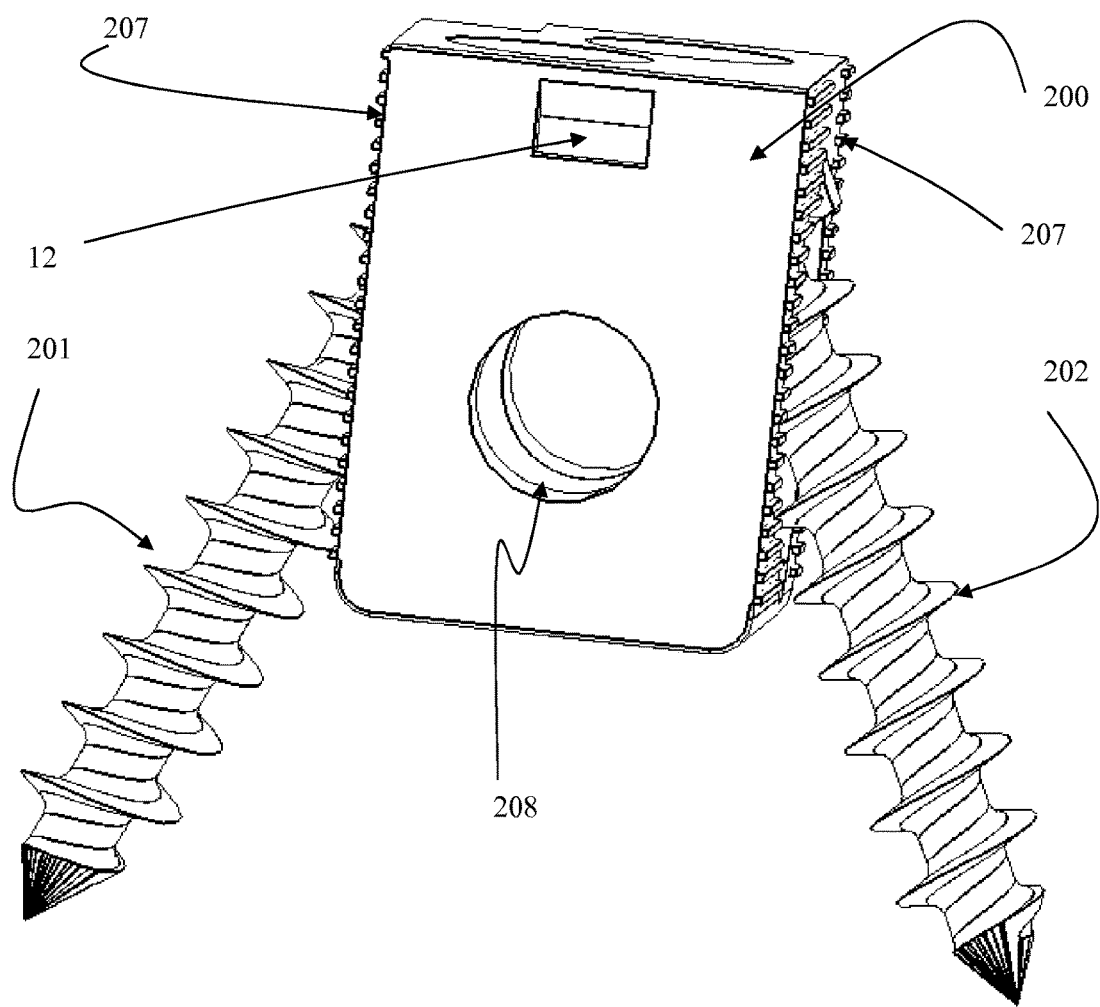
FIG. 5A illustrates a perspective view of an intervertebral cage construct according to an embodiment of the invention.
Figure 5B:
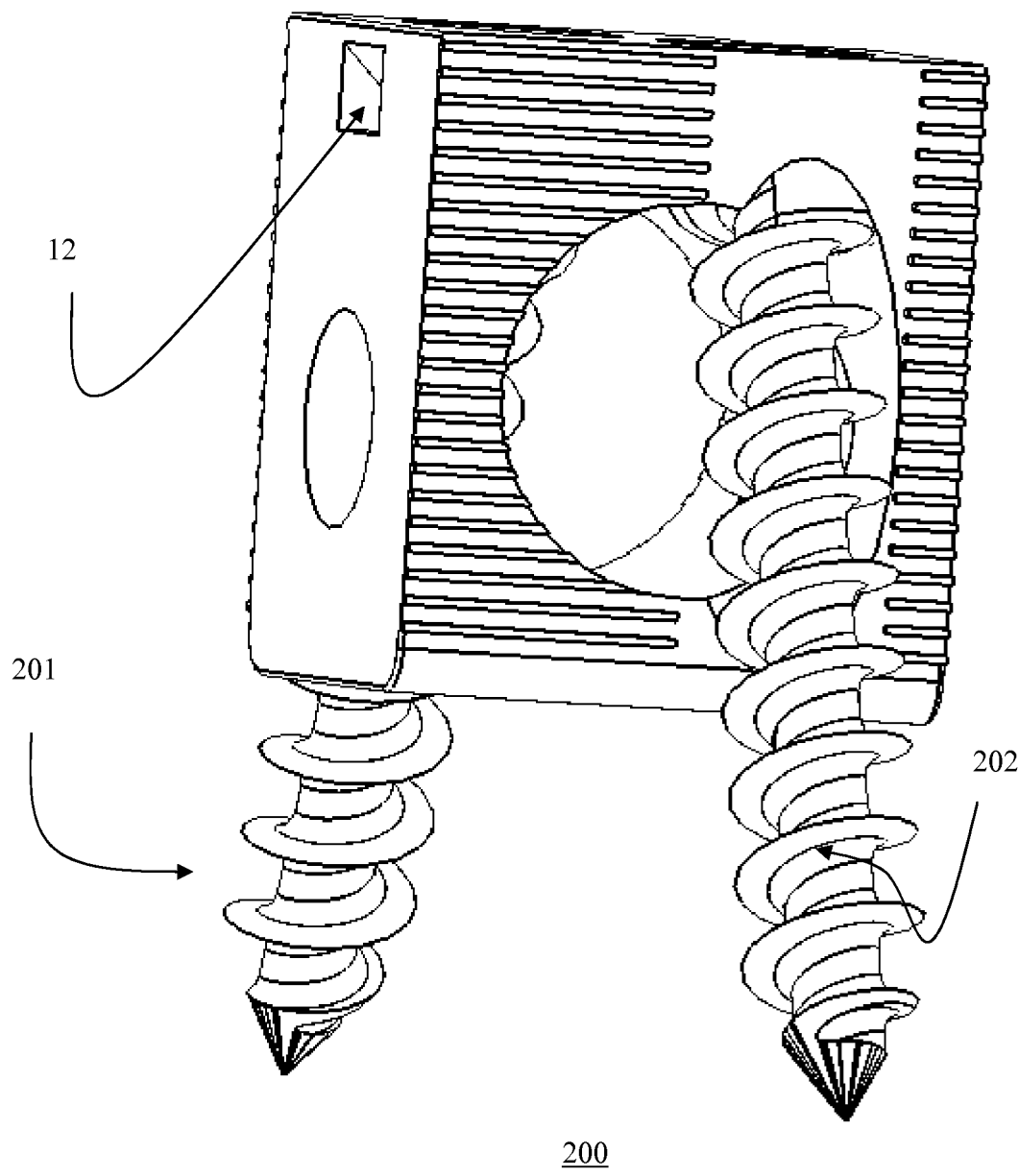
FIG. 5B illustrates another perspective view of an intervertebral cage construct according to an embodiment of the invention.
Figure 5C:
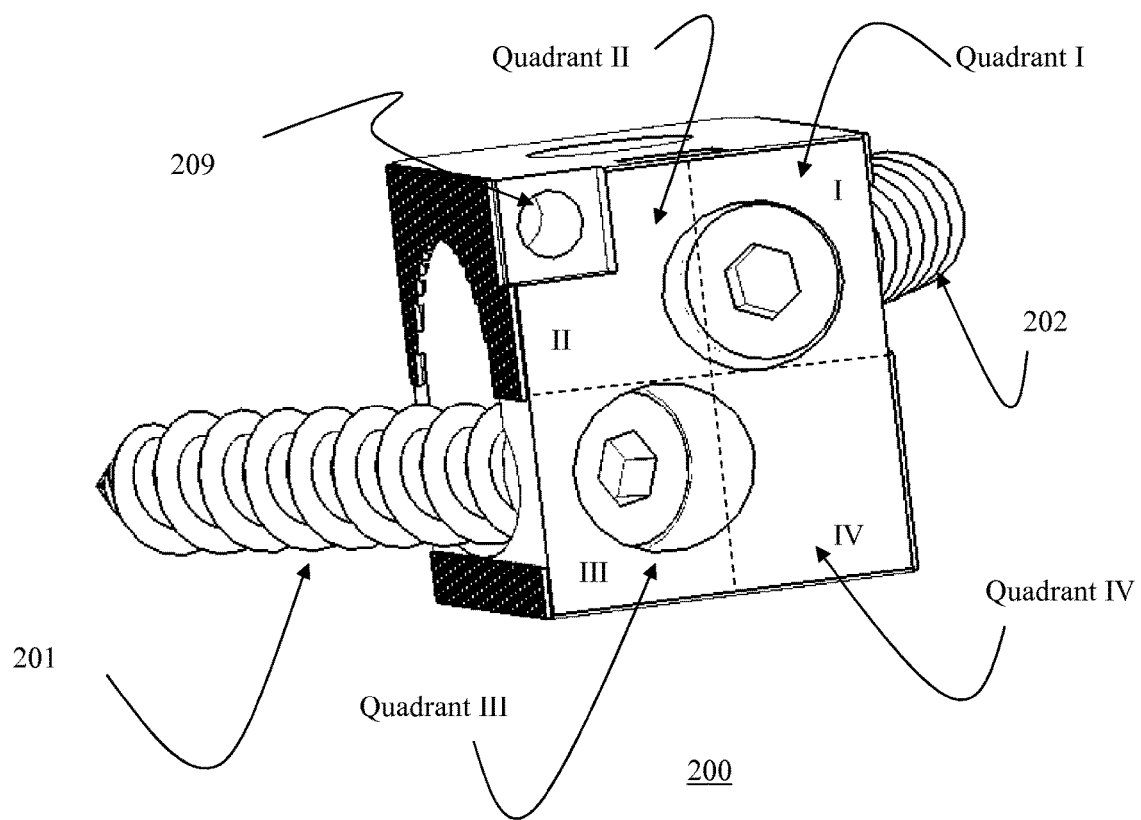
FIGS. 5C(i) and 5C(ii) illustrate top, perspective view of an intervertebral cage construct according to an embodiment of the invention.

FIGS. 5A, 5B, 5C(i), and 5C(ii) illustrate an exemplary embodiment of exemplary cage 200. These features are shown for example purposes, are not limited to the cage 200, and can be incorporated into any cage according to any of the embodiments described herein. As shown in FIGS. 5C(i) and 5C(ii), the screw guides can be positioned within four (4) quadrants I, II, III, IV.

For example, the intervertebral cage can include a wall having an entry opening of the first integral screw guide and an entry opening of the second integral screw guide, wherein the wall of the cage can include four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a majority of an area of the entry opening of the first integral screw guide is in the first quadrant and a majority of an area of the entry opening of the second integral screw guide is in the third quadrant; and the majority of the area of the entry opening of the first integral screw guide is in the second quadrant and the majority of the area of the entry opening of the second integral screw guide is in the fourth quadrant.

In an embodiment, the intervertebral cage can include a wall having an entry opening of the first integral screw guide and an entry opening of the second integral screw guide, wherein the wall has four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a center of the entry opening of the first integral screw guide is in the first quadrant and a center of the entry opening of the second integral screw guide is in the third quadrant; and the center of the entry opening of the first integral screw guide is in the second quadrant and the center of the entry opening of the second integral screw guide is in the fourth quadrant.

Figure 5D:
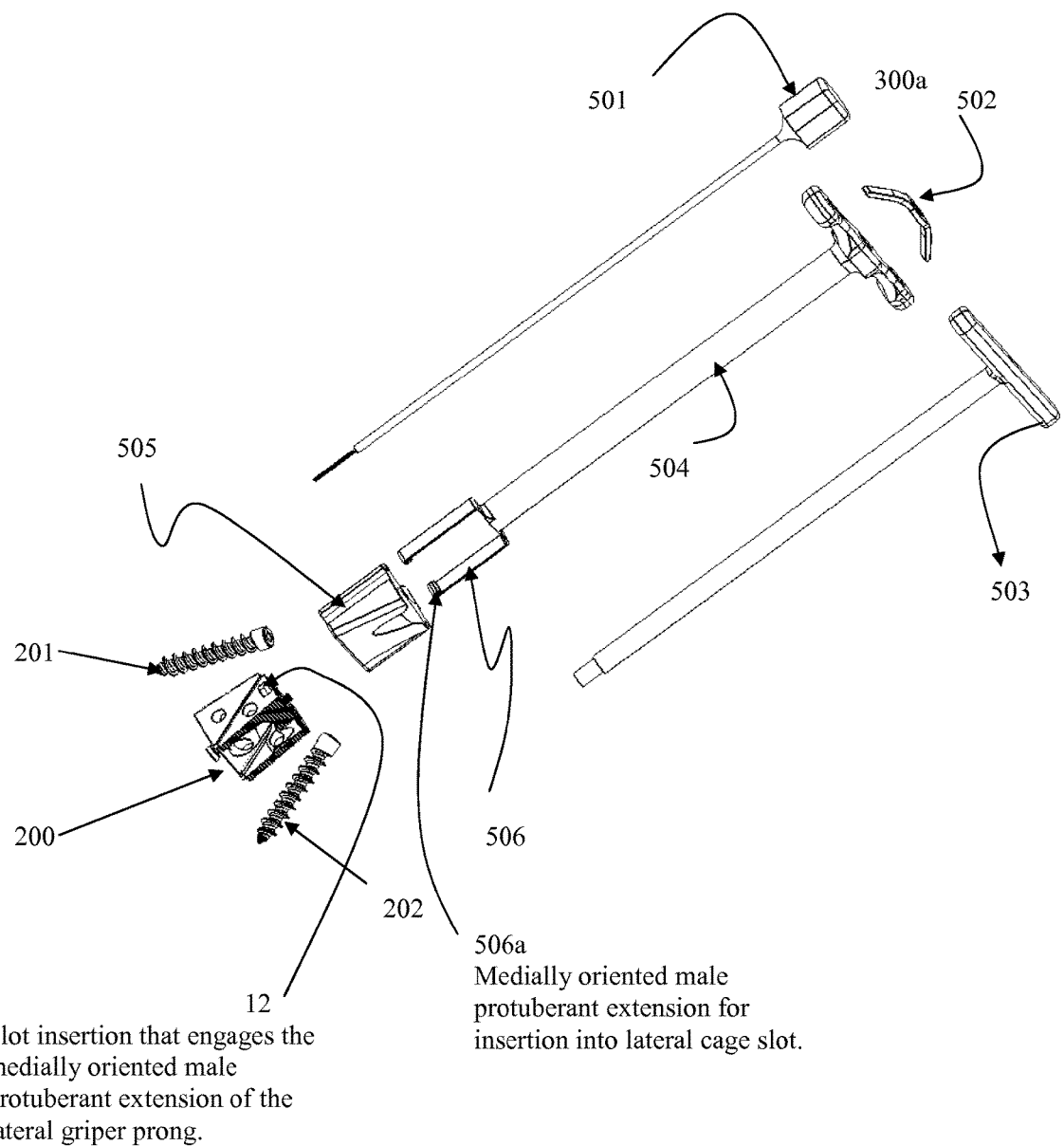
FIG. 5D illustrates a top, perspective, exploded view of a positioning tool/screw guide/box expander.

FIG. 5D illustrates an embodiment of an external drill/screw guide-box expander which assists in screw trajectory of the exemplary cage 200. The cage 200 can be a cage according to any of the embodiments described herein, or an expanding cage, in which case an expanding Allen key component can be used. The device can include, for example, an Allen key 501 (e.g., for an expandable cage), a spring 502, a handle 503, a gripper 504 having a gripper prong 506, which alternatively may include a male protuberance (e.g., a medially oriented mal protuberant extension for insertion into the lateral cage slot 12), and a screw guide 505.

Figure 5E:
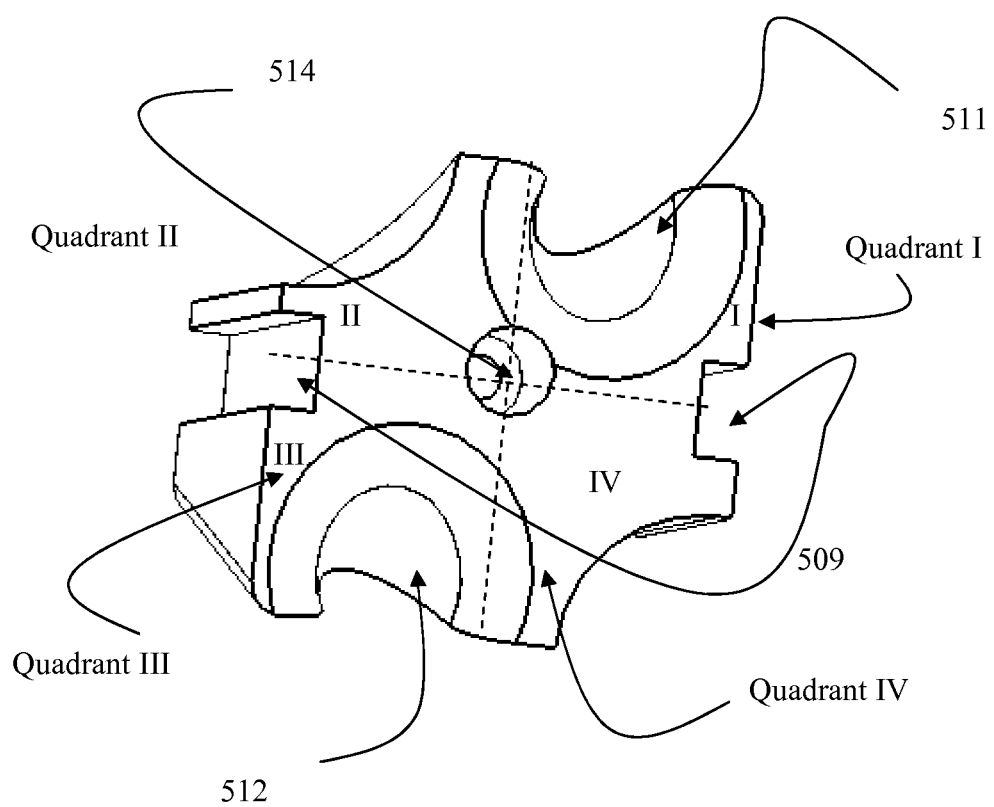
FIG. 5E illustrates a superior oblique perspective view of the positioning tool/drill guide/box expander component.

FIG. 5E illustrates a superior oblique view of the screw guide demonstrating insertions or grooves 509 for gripper prong 506 of the gripper 504 in FIG. 5D, built-in trajectory guides 511, 512 for insertions of screws, and an opening 514 for an Allen key, in instances in which an expandable cage is being used. In an embodiment, the Allen key may not be present when a non-adjustable cage is being used. In another embodiment, the Allen key may be present even when an adjustable cage is being used, such that the tool is universal to various types of cages.

The gripper 504 can include gripper prongs (e.g., medially oriented male protuberant extensions) 506 which insert into grooves 509 of the screw guide 505 and lateral slots (e.g., 12) of a cage, thereby perfectly aligning them.

Hence, according to the exemplary embodiments, a cage can be provided that has internal screw guides which have no gaps, and furthermore an insertion tool can be provided that has an external screw guide that further precisely guides the screws through the external tool screw guide, then into the internal implant screw guide guaranteeing the precise predetermined angulation of the screws. The combination the internal and external screw guides can create a long tunnel for a screw to enable a predetermined trajectory.

It is noted that the same trajectory can be provided by only with the internal box screw guides; however, one of ordinary skill will recognize that having the external screw guides as part of the tool further maintains the precise angle trajectory. The screw guide positions within the four (4) quadrants I, II, III, IV conform to the screw guide positions within the four (4) quadrants I, II, III, IV of the screw box.

With reference to the drawings, it will be understood that an embodiment of the indentations or recesses for the screw holes in any of the exemplary cages can be configured such that the screw heads will rest entirely within a peripheral side of a surface of the top portion of the cage (i.e., top surface). In this embodiment, the direction of the screw tunnel is from an anterior surface to a posterior of the top surface of the cage (i.e., the non-adjacent side).

In another embodiment, the indentations or recesses for the screw holes can be configured such that the screw heads will rest entirely within the peripheral side of the top surface of the cage. In this embodiment, the screw hole guide passes through the anterior-posterior axis of the top surface. The guides core circumference for the screw thread is surrounded by the lateral wall masses, and surrounded by mass from the front and rear surfaces (i.e., walls) of the cage.

In yet another embodiment, the indentations or recesses for the screw holes can be configured such that a recess for the screw holes are entirely within the peripheral side of the top surface of the box. In this embodiment, there is a through-hole for a screw which is counter-bored to keep the screw head within an outer surface boundary of the cage and in a direction to prevent the screw from avoiding the front or rear surfaces of the cage.

In yet another embodiment, the indentations or recesses for the screw holes can be configured such that a recess for the screw holes is entirely within the peripheral side of the front wall of the cage In this embodiment, the tunnel for the screws is such that when the screw first enters, the screw will be surrounded by mass from the lateral sides and mass from the upper and lower sides of the wall. The screw will exit at the posterior end of the peripheral wall.

With reference to the drawings, it will be understood that an embodiment of the indentations or recesses for the screw holes can be configured such that a position of the screws is suitable for posterior lumbar screw holes.

For example, in an embodiment, the screw holes can be diagonal to each other along a transversal line. The transversal line can be defined as the line that would diagonally intersect and bypass the space between the recess for the screw holes.

In another embodiment, the screw holes can be diagonally opposed and lie on a congruent angle to each other from the intersecting transversal line.

In another embodiment, the recess for the screw holes can be diagonal and perpendicular to each other within the outer plane.

In another embodiment, the recess for the screw holes can be diagonal and symmetrically constrained within the outer wall of the cage.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:
    an intervertebral spacing implant including a top wall, a bottom wall, and first and second sidewalls, wherein the intervertebral spacing implant defines:
        an open space between the top, bottom, first, and second sidewalls capable of receiving bone filling for biological bone fusion,
        a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
        a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
    wherein the intervertebral spacing implant further includes:
        a first screw securing mechanism positioned in the top sidewall at the first entry opening of the first internal screw guide so as to extend into the first entry opening; and
        a second screw securing mechanism positioned in the top sidewall at the second entry opening of the second internal screw guide so as to extend into the second entry opening, wherein the first and second screw securing mechanisms are positioned between the first and second internal screw guides with the first screw securing mechanism positioned nearer the second side surface of the top wall than the first side surface of the top wall and with the second screw securing mechanism positioned nearer the first side surface of the top wall than the second side surface of the top wall;
    a first screw having a first screw head and a first threaded body that is sized and configured to be inserted into the first internal screw guide such that the first screw securing mechanism is positioned with respect to the first screw head to restrict the first screw from being removed once the first screw is screwed in place; and
    a second screw having a second screw head and a second threaded body that is sized and configured to be inserted into the second internal screw guide such that the second screw securing mechanism is positioned with respect to the second screw head to restrict the second screw from being removed once the second screw is screwed in place.

2. The apparatus of claim 1, wherein the first and second screw securing mechanisms are press-fit into indentations in the intervertebral spacing implant.

3. The apparatus of claim 1, wherein the first and second screw securing mechanisms prevent rotation of the first and second screws.

4. The apparatus of claim 1, wherein the first and second screw securing mechanisms comprise first and second springs, respectively.

5. The apparatus of claim 1, wherein the first and second screw securing mechanisms prevent back out of the first and second screws by engaging the first and second screw heads, respectively, by applying a securing force to the first and second screw heads.

6. The apparatus of claim 1, wherein removal of the first and second screws requires destroying of the first and second screw securing mechanisms.

7. The apparatus of claim 1, wherein the top wall is continuous with the first and second sidewalls.

8. The apparatus of claim 1, wherein the open space extends from an inner surface of the first sidewall to an inner surface of the second sidewall and extends from an inner surface of the top wall to an inner surface of the bottom wall.

9. The apparatus of claim 1, and further comprising means for facilitating integration and fusion with superior and inferior vertebral bodies.

10. The apparatus of claim 9, wherein the means is positioned at least partially on the first side surface of the top wall between the top surface of the top wall than the first exit opening.

11. The apparatus of claim 1, wherein the first side surface of the top wall is patterned with a plurality of surface features to create a first rough side surface.

12. The apparatus of claim 1, and wherein the locking mechanism comprises titanium.

13. A system comprising the apparatus of claim 1, wherein the intervertebral spacing implant further defines first and second tool slots, wherein the system further comprises:
    a tool having first and second prongs that are sized and configured for grabbing the intervertebral spacing implant at the first and second tool slots, wherein the tool allows access to the first and second internal screw guides while holding the intervertebral spacing implant; and
    a screwdriver sized and configured for driving screws through the first and second internal screw guides while the tool is holding the intervertebral spacing implant between the first and second vertebral bodies.

14. A system comprising the apparatus of claim 1 and means for inserting the apparatus.

15. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:

an intervertebral spacing implant including a top wall, a bottom wall, and first and second sidewalls, wherein the intervertebral spacing implant defines:
an open space between the top, bottom, first, and second sidewalls capable of receiving bone filling for biological bone fusion,
a first tool engagement indentation,
a second tool engagement indentation positioned opposite of the first tool engagement indentation with respect to an axis that bisects the top sidewall,
a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
wherein the intervertebral spacing implant further includes:
a first screw securing mechanism positioned at the first entry opening of the first internal screw guide so as to extend into the first entry opening; and
a second screw securing mechanism positioned at the second entry opening of the second internal screw guide so as to extend into the second entry opening, wherein the first and second screw securing mechanisms are positioned between the first and second internal screw guides with the first screw securing mechanism positioned nearer one of the first and second side surfaces of the top wall than the other of the first and second side surfaces of the top wall and with the second screw securing mechanism positioned nearer one of the first and second side surfaces of the top wall than the other of the first and second side surfaces of the top wall;
a first screw having a first screw head and a first threaded body that is sized and configured to be inserted into the first internal screw guide such that the first screw securing mechanism is positioned with respect to the first screw head to restrict the first screw from being removed once the first screw is screwed in place; and
a second screw having a second screw head and a second threaded body that is sized and configured to be inserted into the second internal screw guide such that the second screw securing mechanism is positioned with respect to the second screw head to restrict the second screw from being removed once the second screw is screwed in place.

16. The apparatus of claim 15, wherein the first and second screw securing mechanisms comprise first and second cantilevered springs, respectively.

17. The apparatus of claim 15, wherein the first and second screw securing mechanisms comprise first and second springs, respectively, wherein ends of the first and second springs are positioned to engage the first and second screw heads when the first and second screws are inserted in the first and second internal screw guides.

18. A system comprising the apparatus of claim 15, wherein the intervertebral spacing implant further defines first and second tool slots, wherein the system further comprises:
a tool comprising:
an elongate shaft;
first and second gripper prongs that are sized and positioned such that the first gripper prong engages the first tool engagement indentation and the second gripper prong engages the second tool engagement indentation when the tool engages the intervertebral spacing implant; and
a tool screw guide defining first and second screw trajectory guides that align with the first and second internal screw guides and control direction of the first and second screws when the tool is engaged with the intervertebral spacing implant and the first and second screws are inserted into the first and second internal screw guides of the intervertebral spacing implant, wherein the first and second gripper prongs extend distally past the tool screw guide on opposite sides of the tool screw guide; and
a screwdriver sized and configured for driving screws through the first and second internal screw guide while the tool is holding the intervertebral spacing implant between the first and second vertebral bodies.

19. The system of claim 18, wherein the first and second screw trajectory guides are defined in opposite sides of the tool screw guide with each of the first and second screw trajectory guides having a partially tubular shape that is curved on one side and open on an opposite side.

20. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:
an intervertebral spacing implant including a top wall, a bottom wall, and first and second sidewalls, wherein the intervertebral spacing implant defines:
an open space between the top, bottom, first, and second sidewalls capable of receiving bone filling for biological bone fusion,
a first slot on an outer surface of the first sidewall,
a second slot on an outer surface of the second sidewall positioned opposite the first slot,
a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
wherein the intervertebral spacing implant further includes:
a first screw securing spring mechanism positioned at the first entry opening of the first internal screw guide so as to extend into the first entry opening; and a second screw securing spring mechanism positioned at the second entry opening of the second internal screw guide so as to extend into the second entry opening, wherein the first and second screw securing spring mechanisms are positioned between the first and second internal screw guides;
a first screw having a first screw head and a first threaded body that is sized and configured to be inserted into the first internal screw guide such that the first screw securing spring mechanism is positioned with respect to the first screw head to restrict the first screw from being removed once the first screw is screwed in place; and
a second screw having a second screw head and a second threaded body that is sized and configured to be inserted into the second internal screw guide such that the second screw securing spring mechanism is positioned with respect to the second screw head to restrict the second screw from being removed once the second screw is screwed in place.

21. The apparatus of claim 20, wherein the open space extends from an inner surface of the first sidewall to an inner surface of the second sidewall and extends from an inner surface of the top wall to an inner surface of the bottom wall.

22. The apparatus of claim 20, and further comprising means for facilitating integration and fusion with superior and inferior vertebral bodies.

23. The apparatus of claim 22, wherein the means is positioned at least partially on the first side surface of the top wall between the top surface of the top wall than the first exit opening.

24. A system comprising the apparatus of claim 20 and means for inserting the apparatus.

* * * * *

UNITED STATES PATENT AND TRADEMARK OFFICE
CERTIFICATE OF CORRECTION

PATENT NO. : 10,376,383 B2
APPLICATION NO. : 15/791484
DATED : August 13, 2019
INVENTOR(S) : Nathan C. Moskowitz et al.

Page 1 of 1

It is certified that error appears in the above-identified patent and that said Letters Patent is hereby corrected as shown below:

On the Title Page

Page 2, Line 19-20 (item (60) Related U.S. Application Data):
Delete "Mar. 11," and insert -- Mar. 10, --, therefor.

Signed and Sealed this
Twenty-sixth Day of May, 2020

Andrei Iancu
*Director of the United States Patent and Trademark Office*